(12) United States Patent
Cornmell et al.

(10) Patent No.: US 9,504,248 B2
(45) Date of Patent: Nov. 29, 2016

(54) ANTIMICROBIAL COMPOSITION

(71) Applicant: Rohm and Haas Company, Philadelphia, PA (US)

(72) Inventors: Robert J. Cornmell, Merseyside (GB); Megan A. Diehl, Line Lexington, PA (US); Stephen Golding, Merseyside (GB); John R. Harp, Knoxville, TN (US); Ian P. Stott, Merseyside (GB); Katherine M. Thompson, Merseyside (GB); Carol L. Truslow, Easton, PA (US)

(73) Assignee: Rohm and Haas Company, Philadelphia, PA (US)

( * ) Notice: Subject to any disclaimer, the term of this patent is extended or adjusted under 35 U.S.C. 154(b) by 104 days.

(21) Appl. No.: 14/363,427

(22) PCT Filed: Dec. 5, 2012

(86) PCT No.: PCT/EP2012/074402
§ 371 (c)(1),
(2) Date: Jun. 6, 2014

(87) PCT Pub. No.: WO2013/083581
PCT Pub. Date: Jun. 13, 2013

(65) Prior Publication Data
US 2014/0350121 A1    Nov. 27, 2014

Related U.S. Application Data

(60) Provisional application No. 61/567,355, filed on Dec. 6, 2011, provisional application No. 61/567,374, filed on Dec. 6, 2011, provisional application No. 61/567,403, filed on Dec. 6, 2011.

(30) Foreign Application Priority Data

Jun. 27, 2012 (EP) .................................... 12173834

(51) Int. Cl.
| | |
|---|---|
| *A01N 31/08* | (2006.01) |
| *A01N 31/04* | (2006.01) |
| *A61K 8/34* | (2006.01) |
| *A61K 31/045* | (2006.01) |
| *A61K 31/05* | (2006.01) |
| *A01N 31/06* | (2006.01) |
| *A61Q 11/00* | (2006.01) |
| *A61Q 17/00* | (2006.01) |

(52) U.S. Cl.
CPC ............... *A01N 31/06* (2013.01); *A01N 31/08* (2013.01); *A61K 8/34* (2013.01); *A61K 8/347* (2013.01); *A61K 31/045* (2013.01); *A61K 31/05* (2013.01); *A61Q 11/00* (2013.01); *A61Q 17/005* (2013.01)

(58) Field of Classification Search
CPC ...... A01N 31/06; A01N 31/08; A61K 8/347; A61K 31/05; A61K 8/34; A61K 31/045; A61Q 11/00; A61Q 17/005
See application file for complete search history.

(56) References Cited

U.S. PATENT DOCUMENTS

| | | | | |
|---|---|---|---|---|
| 5,531,982 | A | * | 7/1996 | Gaffar .................... A61K 8/24 424/49 |
| 5,620,655 | A | * | 4/1997 | Nevermann ........... A01N 31/08 422/28 |
| 2003/0180349 | A1 | | 9/2003 | Franklin |
| 2005/0014827 | A1 | | 1/2005 | Schur |
| 2008/0118591 | A1 | | 5/2008 | Natsch |
| 2008/0194518 | A1 | | 8/2008 | Mookerjee et al. |
| 2015/0087723 | A1 | * | 3/2015 | Cornmell ............... A61K 31/05 514/731 |

FOREIGN PATENT DOCUMENTS

| | | |
|---|---|---|
| WO | 2006/053458 A1 | 5/2006 |
| WO | 2008/126057 A2 | 10/2008 |
| WO | 2010/046238 A1 | 4/2010 |
| WO | 2010/070215 A1 | 6/2010 |

OTHER PUBLICATIONS

Miyazawa et al. Flavour and Fragrance Journal 2003, 18, 398-400.*
Kameoka et al. J. Essent. Oil Res. 1994, 6, 555-560.*
Burger et al. Journal of Chemical Ecology 1999, 25 (9), 2057-2084.*

* cited by examiner

*Primary Examiner* — Sreeni Padmanabhan
*Assistant Examiner* — Irina Neagu
(74) *Attorney, Agent, or Firm* — Kenneth Crimaldi

(57) ABSTRACT

The present invention relates to an antimicrobial composition and a method for disinfection involving the antimicrobial composition. It particularly relates to an antimicrobial composition for personal cleaning, oral care or hard surface cleaning applications. It was found that compositions comprising one or more monosubstituted phenols, terpineol and a carrier provide synergistic antimicrobial action. In a preferred aspect the composition also comprises 1 to 80%-wt of one or more surfactants.

2 Claims, No Drawings

ANTIMICROBIAL COMPOSITION

FIELD OF THE INVENTION

The present invention relates to an antimicrobial composition and a method for disinfection involving the antimicrobial composition. It particularly relates to an antimicrobial composition for personal cleaning, oral care or hard surface cleaning applications.

BACKGROUND TO THE INVENTION

Sanitising and disinfecting soap or cleaning compositions are of great benefit to individuals, since proper use generally may reduce the number of germs and pathogens the individual is exposed to. Thus, such compositions may for instance play an important role in reducing the occurrence and spread of infectious diseases.

Sanitising and disinfecting soap compositions comprising chlorine-based antimicrobial agent such as triclosan are known. Such compositions require a rather long contact time to provide efficacious antimicrobial action. In practice, users, in particular children, do not spend a long time on cleansing and as a result cleaning with such compositions does not provide adequate prevention from surface or topical infection or adequate protection against diseases. The user, in spite of cleaning his hands, is generally likely to end up with relatively inadequate bacterial removal from his skin. Therefore, he may cause contamination of further animate and/or inanimate surfaces and contribute to the spreading of pathogens and consequent diseases. Users in general and children in particular who wash contaminated hands before meals with slow-acting antimicrobial compositions for relatively short time are at risk of contracting diseases.

Similarly in the area of hard surface cleaning, e.g. cleaning of floors, table tops or utensils, the antimicrobial in the compositions are in contact with the substrate for less than a few minutes after which the surface is either wiped off or rinsed with water. These short time scales of cleaning action are ineffective in providing the desired benefit since most known antimicrobials commonly used in such products take many minutes to hours to provide the desired kill of microbes.

Therefore, there is a need of providing a composition that—upon application—provides relatively more efficacious antimicrobial action during a relatively short cleaning period, preferably about 30 seconds or less.

A well-established class of antimicrobially active compounds are phenolic compounds [P A Goddard and K A McCue in "*Disinfection, Sterilisation and Preservation*", ed. S S Block, 5*th* edition, Lippincott, Williams and Wilkins, Philadelphia, 2001 pp. 255-282]. However, not every phenolic compound is suitable as an antimicrobial agent. Moreover, many phenols—even if they are antimicrobially active—may exhibit undesirable side-effects, such as corrosiveness, malodour and irritating or sensitising effects when applied on the human or animal skin. In addition, small changes to molecular structure may in general strongly affect both the desired and the undesired effects in a generally unpredictable way.

A particularly well-known group of phenolic compounds are halogenated phenolics. However, there are concerns about the usage of chlorinated phenols as antimicrobials and herbicides, since they are perceived as pollutants, and are often associated with environmental toxicity, bioaccumulation and low biodegradability [J P Voets et al, *J. Appl. Bact.* vol 40, p. 67-72 (1976); "Chlorophenols in the terrestrial environment" J Jensen, *Reviews of environmental contamination and toxicology*, Vol 146 pp 25-51 (1996)).

WO 2010/046238 A1 describes an effective antimicrobial composition which provides rapid kill of pathogenic bacteria and which comprises 0.01 to 5% by weight of thymol, 0.01 to 5% by weight of terpineol and a carrier. WO 2010/046238 A1 also discloses a method of disinfecting a surface including the step of applying the above composition to the surface.

EP 0 791 362 A2 discloses a composition comprising a peroxygen bleach, from 0.003% to 5% by weight of the total composition of a cyclic terpene or a derivative thereof and from 0.003% to 5% by weight of the total composition of a phenolic compound. The composition can be used to disinfect various surfaces, including animate and inanimate surfaces. It was found that the use of a cyclic terpene and/or a derivative thereof (e.g. eucalyptol) together with a phenolic compound (e.g. eugenol, carvacrol, ferulic acid) results in a synergistic effect on disinfecting performance. Suitable cyclic terpenes include any mono- or polycyclic compound including at least one isoprenic unit, preferably 1 or 2, said isoprenic unit may comprise one or more hetero atoms, preferably, oxygen, and said isoprenic unit may be substituted at any carbon by H, a linear or branched, saturated or unsaturated hydrocarbon chain, an alkoxylated hydrocarbon chain, or an aryl chain having from 1 to 20 carbon atoms, more preferably from 1 to 4. Highly preferred cyclic terpenes or derivatives thereof are limonene, menthol, eucalyptol, terpineol and mixtures thereof.

The phenolic compounds of the composition according to EP 0 791 362 A2 have the following formula:

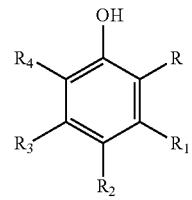

wherein R, R1, R2, R3, R4 independently are H, a linear or branched, saturated or unsaturated hydrocarbon chain having from 1 to 20 carbon atoms, an alkoxylated hydrocarbon chain according to the formula Ra(A)n wherein Ra is a linear or branched, saturated or unsaturated hydrocarbon chain having from 1 to 20 carbon atoms, wherein A is butoxy, propoxy and/or ethoxy, and n is an integer of 1 to 4, or an aryl chain having from 1 to 20 carbon atoms. Eugenol, carvacrol and ferulic acid are preferred phenolic compounds. EP 0 791 362 A2 also discloses a process of disinfecting an inanimate surface, in particular fabrics, with the above composition. In different modes of fabric disinfecting, contacting times from 1 to 30 minutes, or from 1 minute to 24 hours are preferred.

U.S. Pat. No. 6,152,152 discloses a method for washing dishes, which comprises applying to an absorbent implement an undiluted liquid dishwashing composition comprising a) from 10% to 60% by weight of a surfactant, b) from 1% to 15% by weight of a hydrotrope selected from the group consisting of salts of cumene sulfonate, toluene sulfonate, xylene sulfonate, benzene sulfonate and mixtures thereof; and c) from 0.1% to 3% by weight of the total composition of an unsaturated aliphatic terpene alcohol or derivative, and d) a phenolic compound. The phenolic compound is of the same formula as given for EP 0 791 362

A2 above. The preferred aliphatic terpene alcohol is geraniol; preferred phenolic compounds are eugenol, thymol, and mixtures thereof. It was found that such dishwashing compositions can fulfil the purpose of reducing or eliminating bacterial growth on absorbing dish implements. To achieve this, the dish implement is preferably contacted, e.g. soaked with neat product and left to dry.

WO 04/035723 is directed to concentrated cleaning and/or disinfecting compositions which bloom when diluted in water. It discloses a hard surface cleaning concentrate composition comprising: a) from about 0.05 to about 10 wt % of a non-cationic antimicrobial agent; b) from about 1 to about 20 wt % of a water soluble organic solvent c) from about 1 to about 20 wt % of an anionic soap surfactant; d) from about 1 to about 15 wt % of a hydrocarbon diluent; e) from about 0.001 to about 20 wt % of pine oil which is at least 60% terpene alcohols; f) optionally, from about 0 to about 10 wt % of optional materials selected from dyes, colorants, pH stabilizers and buffers, non-ionic surfactants, fragrance/fragrance enhancers, viscosity modifiers, insect repellants, and light stabilizers; and g) the balance being water. Phenol based non-cationic antimicrobials are preferred. Important constituents of the pine oil include terpineol. It is shown that a composition comprising 1.50 wt % of aromatic hydrocarbons (Aromatic 200), 1.00 wt % of Pine Oil 80, 1.50 wt % of PCMX (p-chloro-m-xylenol), 2.00 wt % of isopropyl alcohol, 20 wt % of NaCOS (sodium castor oil soap—40%), 0.40 wt % of insect repellant. 73.60 wt % water and added dye provides a Log 10 reduction value of greater than 3 In a microbial reduction suspension test, after a contact time of 15 seconds, using 1:60 to 1:100 dilutions of the composition in water and one part of organism suspension (*Staphylococcus aureus* or *Salmonella choleraesuis*).

FR 2 697 133 discloses biocidal and/or biostatic compositions, comprising mono-oxygenated sesquiterpenes of general formula $C_{15}H_xO$, wherein x is between 20 and 26 and aromatic compounds.

Despite the general availability of antimicrobial compounds and compositions, there remains a continuous need to find alternative antimicrobial compositions and active compounds that are suitable for use in such compositions. In particular, alternative compositions providing fast antimicrobial action remain highly desirable in view of current consumer habits. Such alternatives may reduce the dependency on current raw materials. Moreover, in the field of antimicrobials, the availability of alternatives may reduce the risk of development of microbial resistance or insensitivity to particular antimicrobial compounds.

In addition, there is a continued need to reduce the total amount of active Ingredients required in such an antimicrobial composition. This need may for instance be driven by the desire for cost-efficiency, because such compositions are particularly relevant to developing countries. Moreover, reducing the amounts may also be beneficial for environmental reasons.

A particular problem of certain antimicrobial actives, and especially some phenolic compounds such as thymol is that they are generally well-perceptible due to their olfactory properties. Although the latter may—at least for some species—be appreciated in certain fragrance compositions, they are considered too intense by some users when they are applied at concentrations efficacious in rapid disinfection. Additionally, a lower concentration of odoriferous compounds or the availability of antimicrobial compounds that are less or not odoriferous allows greater flexibility to the manufacturer in providing alternative scents to his composition at lower doses. Hence there is a need to provide alternative antimicrobial compositions and methods that preferably require lower concentrations and/or have a more acceptable sensory profile.

In view of the above-observed problems and drawbacks of the prior art, it is an object of the present invention to provide alternative antimicrobial compositions, in particular antimicrobial compositions that do not depend on halogenated phenols for their antimicrobial efficacy.

It is a particular object of the invention to provide such compositions, requiring a lower dose of antimicrobial compounds.

Similarly, it is an object of the present invention to provide an antimicrobial composition in which the olfactory contribution of the antimicrobially active compounds is reduced or in which the active compound contributes to providing a consumer-acceptable or even consumer-appreciated scent.

It is another particular object of the invention to provide an antimicrobial composition that contributes to reducing the required contact time in a method for disinfection of a surface.

In particular, it is an object of the invention to provide an antimicrobial composition which gives improved disinfection during cleansing of surfaces of the human body, such as the skin and the oral cavity.

It is yet another object of the present invention to provide an alternative method for sanitising and/or disinfecting, in particular of surfaces.

It is a further object of the invention to provide a method for disinfection with a reduced disinfection time. More specifically, it is an object of the invention to provide a method, wherein the disinfection time of the method is less than 300 seconds, preferably less than 60 seconds, and more preferably less than 15 seconds.

In particular, it is an object of the invention to provide a method for disinfection that gives improved disinfection during cleansing of surfaces, in particular hard surfaces, or surfaces of the human body, such as the skin and the oral cavity.

SUMMARY OF THE INVENTION

We have now found that one or more of the above objects are met by the present invention. Thus, we have found that compositions comprising selected monosubstituted phenols and terpineol provide synergistic antimicrobial action. Such compositions provide similar or more efficacious anti-microbial action, at similar or lower concentrations when compared to thymol and alpha-terpineol. In particular, we found that combinations of monosubstituted phenols and terpineol according to this invention are capable of very fast antimicrobial action. For instance, we found that complete microbial inactivation could be effected with compositions according to the present invention after a contact time of only 15 seconds. Moreover, the compositions according to the present invention do not rely on the presence of halogenated phenols for their antimicrobial efficacy.

Accordingly, in a first aspect the invention provides an antimicrobial composition comprising:
  i. 0.001 to 5% by weight of one or more monosubstituted phenols,
  ii. 0.001 to 5% by weight of terpineol, and
  iii. a carrier
  wherein the one or more monosubstituted phenols have the following structure

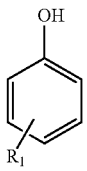

wherein
the substituent $R_1$ is selected from the group consisting of
linear $C_3$ to $C_5$ alkyl,
isopropyl
branched $C_4$ alkyl,
linear $C_3$ to $C_3$ alkenyl,
linear $C_4$ or $C_5$ alkadienyl,
branched $C_4$ alkenyl,
cyclopentyl,
cyclopentenyl,
cyclohexyl,
cyclohexenyl,
phenyl, and
benzyl;
and wherein
the terpineol is selected from the group consisting of alpha-terpineol, beta-terpineol, gamma-terpineol, delta-terpineol, 4-terpineol, and mixtures thereof.

According to a second aspect of the invention, there is provided a method of disinfecting a surface comprising the steps of
a. applying a composition according to the invention on to the surface; and
b. removing the composition from the surface.

In a third aspect, the invention provides the use of a composition according to the invention for improved hygiene.

DETAILED DESCRIPTION OF THE INVENTION

For the avoidance of doubt, any feature of one aspect of the present invention may be utilised in any other aspect of the invention. The word "comprising" is intended to mean "including" but not necessarily "consisting of" or "composed of." Thus, the term "comprising" is meant not to be limiting to any subsequently stated elements but rather to optionally also encompass non-specified elements of major or minor functional importance. In other words, the listed steps or options need not be exhaustive. Whenever the words "including" or "having" are used, these terms are meant to be equivalent to "comprising" as defined above. It is noted that the examples given in the description below are intended to clarify the invention and are not intended to limit the invention to those examples per se.

Except in the examples, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated.

Phenol in its strict sense refers to hydroxybenzene ($C_6H_5OH$), but where appropriate the word phenol may in its wider meaning as understood by the skilled person also refer to a member of the class of compounds which comprise at least one such a characteristic hydroxybenzene moiety.

Throughout this description, the term disinfection refers to reduction of the number of viable microorganisms in a given medium or on a given surface by physical or chemical means. Typically, disinfection involves the destruction or inactivation of said microorganisms. Both animate and inanimate media and surfaces are contemplated.

The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mould), bacteria and algae.

The antimicrobial composition comprises one or more monosubstituted phenols, terpineol and a carrier. Various components of the antimicrobial composition are described below.

The compositions of the present Invention are preferred for non-therapeutic use, and more particularly preferred for use in cleaning surfaces of human body including skin, hair or oral cavity or for hard surface cleaning applications.

Monosubstituted Phenols

The antimicrobial composition according to the invention comprises 0.001 to 5% by weight of one or more monosubstituted phenols. The composition comprises preferably 0.005 to 4.5 wt-%, more preferably 0.01 to 4 wt-%, even more preferably 0.02 to 3 wt-%, yet more preferably 0.03 to 2 wt-%, still more preferably 0.04 to 1 wt-%, even more preferably 0.05 to 0.75 wt-% and still more preferably 0.1 to 0.5 wt-% of the one or more monosubstituted phenols. In compositions intended to be diluted before application, the minimum preferred concentrations of the one or more monosubstituted phenols can be higher. For example, when washing hands with water and a composition according to the invention, the lather produced, typically is a 50 wt % dilution of the original composition. Similarly, in body wash situations, soap bars or soap liquids are typically diluted until about 8 wt % soap in water, corresponding to an approximately tenfold dilution of the product. Therefore, compositions according to the invention intended for dilution upon use preferably comprise 0.05 to 4.5 wt-%, more preferably 0.1 to 4 wt-%, even more preferably 0.2 to 3 wt-%, still more preferably 0.4 to 1 wt-%, and still more preferably 0.5 to 1 wt-% of the one or more monosubstituted phenols. Thus, the concentration of the one or more monosubstituted phenols in the antimicrobial composition is preferably such that, when the composition is diluted or dissolved with a suitable medium during use, the concentration in the diluted or dissolved mixture is still sufficient to be antimicrobially efficacious.

The monosubstituted phenol may be a single compound or may be a mixture of the monosubstituted phenols as detailed below. In certain preferred embodiments, mixtures of monosubstituted phenols are preferred, since such mixtures may show increased antimicrobial activity against a wider range of microbes. On the other hand, for reasons including e.g. control over the formulation, it is preferred that in case the composition according to the invention comprises a mixture of such monosubstituted phenols, the mixture preferably comprises at least 30%, more preferably at least 50%, even more preferably at least 70% and still more preferably at least 90% by weight of one monosubstituted phenol with respect to the total weight of the monosubstituted phenols.

At concentration ranges of the monosubstituted phenols below the lower concentration limits of the monosubstituted phenols, the desired fast acting antimicrobial kinetics in combination with terpineol would not be met. At concentrations higher than the higher preferred concentrations of monosubstituted phenols, when in combination with a terpineol, while the kinetics of action would not be compromised, the present inventors have found that unlike in therapeutic/pesticidal/herbicidal applications where sensorial aspects are not critical, in the present application, which is preferably a personal cleaning, oral care or hard surface cleaning applications, the product is in contact with hands, mouth or other body parts, the sensorial aspects including smell and skin feel would be compromised.

The one or more monosubstituted phenols have the following structure

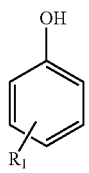

wherein the substituent $R_1$ is selected from the group consisting of linear $C_3$ to $C_5$ alkyl, isopropyl, branched $C_4$ alkyl, linear $C_3$ to $C_5$ alkenyl, linear $C_4$ or $C_5$ alkadienyl, branched $C_4$ alkenyl, cyclopentyl, cyclopentenyl, cyclohexyl, cyclohexenyl, phenyl, and benzyl.

All positional isomers of the monosubstituted phenols are contemplated. The $R_1$ group can be substituted to any of the carbons of the phenol ring. Thus, with $R_1$ is linear $C_5$ alkyl, for example, the one or more monosubstituted phenols can be selected from 2-pentyl phenol, 3-pentyl phenol, and 4-pentyl phenol.

The substituent $R_1$ is preferably selected from the group consisting of linear $C_3$ to $C_5$ alkyl, branched $C_4$ alkyl, linear $C_3$ to $C_5$ alkenyl, linear $C_4$ or $C_5$ alkadienyl, branched $C_4$ alkenyl, cyclopentyl, cyclopentenyl, cyclohexyl, cyclohexenyl, phenyl, and benzyl.

More preferably, the substituent $R_1$ is a branched $C_4$ alkyl or a branched $C_4$ alkenyl group, and even more preferably, the substituent $R_1$ is selected from the group consisting of tert-butyl, sec-butyl, and isobutyl.

Alternatively, in some embodiments, the substituent $R_1$ preferably is selected from the group consisting of cyclopentyl and cyclohexyl. More preferably, $R_1$ is cyclopentyl. Still more preferably, the monosubstituted phenol is 2-cyclopentylphenol. This preference, which is for instance relevant to embodiments directed to treatment of the skin, is based on the favourable toxicological profile of these compounds.

Alternatively, it is particularly preferred that the one or more monosubstituted phenols are selected from the group consisting of 4-propylphenol, 4-n-butylphenol, 4-pentylphenol, 2-tert-butylphenol, 3-tert-butylphenol, 2-sec-butylphenol, 4-sec-butylphenol, 2-cyclopentylphenol, 4-cyclopentylphenol, 2-cyclohexylphenol, 2-(prop-1-enyl)phenol, (more preferably (E)-2-(prop-1-enyl)phenol, 2-allylphenol, 3-phenylphenol, 2-benzylphenol, and 4-benzylphenol.

Alternatively, it is similarly preferred that the one or more monosubstituted phenols are selected from the group consisting of 2-n-propyl phenol, 3-n-propyl phenol and 4-n-propyl phenol.

It is even more preferred that the one or more monosubstituted phenols are selected from the group consisting of 2-tert-butylphenol, 3-tert-butylphenol, 2-sec-butylphenol, 4-sec-butylphenol, 2-cyclopentylphenol, 4-cyclopentylphenol, and 2-cyclohexylphenol.

It is still more preferred that the one or more monosubstituted phenols are selected from the group consisting of 2-tert-butylphenol, 3-tert-butylphenol, 2-sec-butylphenol, and 4-sec-butylphenol.

In case the one or more monosubstituted phenols are phenylphenols, it is preferred that they are selected from 2-phenyl phenol and 3-phenyl phenol.

In another preferred embodiment, the one or more monosubstituted phenols are preferably selected from the group consisting of 2-n-propylphenol, 4-n-butylphenol, 4-sec-butylphenol, 2-cyclopentylphenol, and 4-cyclopentyl phenol.

In case the carrier or the dissolution medium during later application is water-based, it can be advantageous if the one or more monosubstituted phenols are sufficiently water-soluble. The monosubstituted phenols are sufficiently water-soluble if they are soluble to at least the minimum concentration required in the antimicrobial composition according to the invention.

The unsaturated $R_1$-substituents according to the invention, for example the alkenyl, alkadienyl, and cycloalkenyl substituents, comprise a C—C double bond, which may take any position in the substituent. Thus, the cyclopentenyl substituents, for instance include (cyclopent-1-en-1-yl)-, (cyclopent-2-en-1-yl), and (cyclopent-3-en-1-yl)-substituents.

Several non-limiting examples of the structures of the one or more monosubstituted phenols according to the present invention are provided in Table 1.

TABLE 1

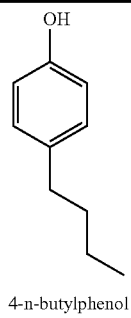

4-n-butylphenol

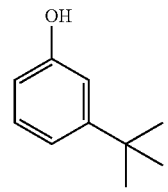

3-tert-butylphenol

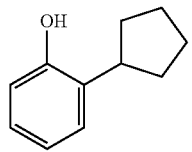

2-cyclopentylphenol

TABLE 1-continued

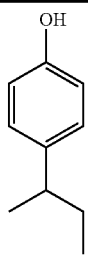

4-sec-butylphenol

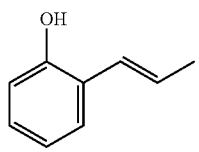

(E)-2-(prop-1-enyl)-phenol

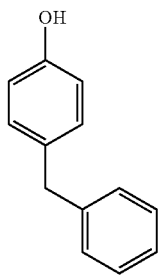

4-benzylphenol

Advantageously, some compounds according to the invention have a weaker odour, when compared to that of thymol, or an odour which can be more appreciable to the consumer, when dosed into the compositions according to the invention at efficacious levels. This benefit especially applies to for instance 2-(prop-1-enyl)phenol, 4-propylphenol, 4-n-butylphenol, 4-pentylphenol, 4-benzylphenol, 2-cyclopentylphenol, and 4-cyclopentylphenol. Therefore, these are preferred compounds.

Mixtures of preferred monosubstituted phenols are also preferred. Where applicable, the different stereoisomers of the monosubstituted phenols are contemplated. Thus, compositions comprising enantiomerically pure compounds, racemic mixtures and other mixtures of different stereoisomers of the monosubstituted phenols are equally preferable, unless indicated otherwise in this application.

Without wishing to be bound by theory, it is believed that the synergistic mode of antimicrobial action of the monosubstituted phenols according to the present invention in combination with terpineol is similar for the different respective monosubstituted phenols.

The extent to which the monosubstituted phenols according to the present invention are soluble in water or in organic solvents may be suitably expressed by the logarithm of the octanol/water partitioning coefficient, log {P}. This partition coefficient s a measure for the distribution of a solute between water and octanol at equilibrium. The value of the partitioning coefficient may also be predicted using computational methods. A commonly used predicted value is the so-called A log P value. A definition and preferred method of calculation of A log P values is provided in A. K. Ghose, V. N. Viswanadhan, and J. J. Wendoloski, *J. Phys. Chem. A*, vol 102, pag. 3762 (1998). Due to the standardised calculation as described by Ghose et al, A log P values of different compounds can be compared with one another and used to assess the similarity of or difference between different compounds. For instance, phenol has an A log P value of 1.59 and thymol has an A log P value of 3.27. Such comparison can also extend to other properties that are believed to be related to the same molecular properties that underlie the value of A log P. Though not wishing to be bound by theory in this respect, it is believed that there is some correlation between A log P and the antimicrobial efficacy of the monosubstituted phenols according to the present invention. Therefore, the monosubstituted phenols according to the present invention preferably have an A log P value of between 2.0 and 4.5, more preferably between 2.2 and 4.4, even more preferably between 2.4 and 4.1 and still more preferably between 2.5 and 4.0.

Suitable monosubstituted phenols according to the present invention may be commercially sourced or obtained via synthetic chemical methods. Such methods are generally well-known to the person skilled in the art. For example, alkyl substituted phenols may be synthesised by Friedel Crafts reaction of phenol with an olefin in the presence of an acid catalyst such as sulphuric acid, acid activated silicas, boron trifluoride or aluminium chloride. Arylation of phenol with benzene can be achieved under similar reaction conditions, sometime termed the Scholl reaction [J March, "Advanced Organic Chemistry: Reactions, Mechanisms and Structure", 4$^{th}$ edition John Wiley, New York, 1992, pages 534-539; H. Fiege, H-W. Voges, T. Hamamoto, S. Umemura. T. Iwata, H. Miki, Y. Fujita, H-J. Buysch., D. Garbe and W. Paulus, "Phenol Derivatives" in Ullmann's Encyclopedia of Industrial Chemistry, Wiley-VCH, Volume 26, page 526, 2000]

Terpineol

The antimicrobial composition according to the invention comprises 0.001 to 5% by weight of terpineol. The composition comprises preferably 0.005 to 4.5 wt-%, more preferably 0.01 to 4 wt-%, even more preferably 0.02 to 3 wt-%, yet more preferably 0.03 to 2 wt-%, still more preferably 0.04 to 1 wt-%, still more preferably 0.05 to 0.75 wt-% and even more preferably 0.1 to 0.5 wt-% of terpineol. In compositions intended to be diluted before application, the minimum preferred concentrations of the terpineol can be higher, for the same reasons as for the monosubstituted phenols. Therefore, compositions according to the invention intended for dilution upon use preferably comprise 0.05 to 4.5 wt-%, more preferably 0.1 to 4 wt-%, even more preferably 0.2 to 3 wt-%, still more preferably 0.4 to 1 wt-%, and still more preferably 0.5 to 1 wt-% of the terpineol. Any of these concentration ranges for the terpineol is preferably combined with any of the concentration ranges for the one or more monosubstituted phenols specified above. Therefore, the antimicrobial composition according to the invention for example comprises:

a. 0.01 to 0.4% by weight of the one or more monosubstituted phenols: and b. 0.05 to 1% by weight of the terpineol.

The terpineol may be a single compound or may be a mixture of the terpineol isomers as detailed below. Mixtures of terpineols are preferred, since such mixtures may show increased antimicrobial activity against a wider range of microbes. In case the composition according to the invention comprises such a mixture of terpineols, the mixture preferably comprises at least 30%, more preferably at least 50%, even more preferably at least 70% and still more preferably at least 90% by weight of one terpineol isomer with respect to the total weight of the terpineol. Preferably, said one terpineol isomer is alpha-terpineol. The preferred concentrations ranges of the terpineol are important for the same reasons as the preferred concentration ranges of the one or more monosubstituted phenols in meeting the desired fast acting antimicrobial kinetics while not being sensorially unpleasant when used in products for personal cleaning, oral care or hard surface cleaning applications.

Terpineol Isomers

Terpineol exists as different isomers, which all are considered terpineols. The terpineol is selected from the group consisting of alpha-terpineol, beta-terpineol, gamma-terpineol, delta-terpineol, 4-terpineol, and mixtures thereof. More preferably, the terpineol is selected from the group consisting of alpha-terpineol, beta-terpineol, gamma-terpineol, delta-terpineol, and mixtures thereof. In nature, the isomeric compounds alpha-terpineol, beta-terpineol and gamma-terpineol are among the most abundant terpineols and often occur together in mixtures. Therefore even more preferably, the terpineol is selected from the group consisting of alpha-terpineol, beta-terpineol, gamma-terpineol, and mixtures thereof. The structures of these isomers are schematically depicted in Table 2 below.

TABLE 2

Terpineol isomers

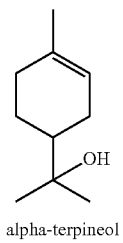

alpha-terpineol

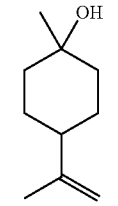

beta-terpineol

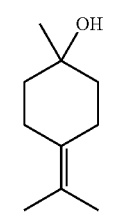

gamma-terpineol

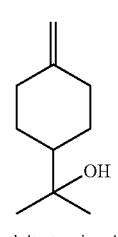

delta-terpineol

TABLE 2-continued

Terpineol isomers

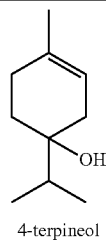

4-terpineol

Where applicable, the different stereoisomers of these terpineol isomers are contemplated. For instance, cis-beta-terpineol and trans-beta-terpineol are both contemplated. Thus, compositions comprising enantiomerically pure radicals, racemic mixtures and other mixtures of different stereoisomers are equally preferable.

These terpineols are all members of the menthenol class of compounds [A L Gunatilaka, Natural products in Plants: Chemical Diversity in the Wiley Encyclopedia of Chemical Biology, pp 1-17 and E Breitmaier, Terpenes: flavors, fragrances, pharmaca, pheromones; p. 17, Wiley-VCH, 2006], also termed oxytetrahydrocymenes [F Heusler, The Chemistry of the Terpenes, trans. F J Pond, P Blakistons's son & Co, Philadelphia, 1902, p. 21] which may be defined as monohydroxy alcohol derivatives of p-menthene, with the generic formula $C_{10}H_{17}OH$. Combinations of these terpineol isomers are often found together in nature, because it is generally believed that their biosyntheses proceed via closely related synthetic pathways. Without wishing to be bound by theory, it is believed that the mode of antimicrobial action of these terpineol isomers in combination with the monosubstituted phenols according to the present invention is similar.

The terpineols may also be referred to by the alternative names as detailed below in Table 3.

TABLE 3

| alpha-terpineol | p-menth-1-en-8-ol | 2-(4-methylcyclohex-3-en-1-yl)propan-2-ol |
| --- | --- | --- |
| beta-terpineol | p-menth-8-en-1-ol | 1-methyl-4-(prop-1-en-2-yl)-cyclohexanol |
| gamma-terpineol | p-menth-4(8)-en-1-ol | 1-methyl-4-(propan-2-ylidene)-cyclohexanol |
| delta-terpineol | p-menth-1(7)-en-8-ol | 2-(4-methylenecyclohexyl)propan-2-ol |
| 4-terpineol | p-menth-1-en-4-ol | 1-isopropyl-4-methylcyclohex-3-enol |

Terpineol may be added to the antimicrobial composition in purified form. Alternatively pine oil comprising terpineol may be added to the antimicrobial composition while ensuring that terpineol is present in the desired concentration in the composition of the present invention.

Carrier

The antimicrobial composition according to the invention comprises a carrier. The carrier is preferably selected from the group consisting of water, oil, solvent, inorganic particulate material, starch, air and mixtures thereof. The carrier is preferably from 0.1 to 99% by weight of the composition. The antimicrobial composition may be in form of a solid, liquid, gel, paste or soft solid and the carrier may be selected by a person skilled in the art depending on the format of the antimicrobial composition.

Examples of inorganic particulate materials include clay, talc, calcite, dolomite, silica, and aluminosilicate. Examples of oils include mineral oils, oils of biological origin (e.g. vegetable oils), and petroleum-derived oils and waxes. The oils of biological origin are preferably triglyceride-based. Preferably, the carrier oil is not a perfume oil. Thus, the carrier oil preferably does not substantially contribute to the odour of the composition, more preferably it does not contribute to that odour. Examples of solvents include alcohols, ethers and acetone. The starch may be natural starch obtained from food grains or may be a modified starch.

In certain preferred embodiments, suitable solvents include, for example, water; glycols, including ethylene glycol, propylene glycol, diethylene glycol, dipropylene glycol, polyethylene glycol, and polypropylene glycol; glycol ethers; alcohols, such as methanol, ethanol, propanol, phenethyl alcohol and phenoxypropanol; ketones, including acetone and methyl ethyl ketone; esters, including ethyl acetate, butyl acetate, triacetyl citrate, and glycerol triacetate; carbonates, including propylene carbonate and dimethyl carbonate; and mixtures thereof. It is preferred that the solvent is selected from water, glycols, glycol ethers, esters and mixtures thereof. In certain preferred embodiments, suitable solid carriers include, for example, cyclodextrin, silicas, diatomaceous earth, waxes, cellulosic materials, alkali and alkaline earth (e.g., sodium, magnesium, potassium) metal salts (e.g., chloride, nitrate, bromide, sulfate) and charcoal.

Air can for instance be used as a carrier when the monosubstituted phenols according to the invention and/or the terpineol are atomised or otherwise dispersed as a fine mist.

Particularly preferred carriers are water or oil/solvent and even more preferred is a carrier that is a mixture of water and oil. Thus, in many of the envisaged applications like personal care/washing, oral care and hard surface cleaning, the antimicrobial composition may be formulated with either an aqueous base or an oil/solvent base. Compositions with an aqueous base (water being the carrier), can also for instance be products in gel format. Compositions with an oil/solvent base can for instance be products in anhydrous stick form or propellant-containing products.

Thus, the antimicrobial composition can for instance, preferably be an antimicrobial anhydrous stick personal care composition on an oil/solvent base wherein the composition has a water content of less than 0.01% by weight, and wherein the composition preferably is free of water. Alternatively, the antimicrobial composition can for instance, preferably be an antimicrobial propellant-drivable personal care composition, also comprising a propellant. Air can also be used as propellant, for instance in the form of compressed or liquefied air.

However, the most preferred product format has an emulsion base (water and/or oil being the carrier) or is capable of forming an emulsion upon dilution, e.g. soap products in liquid, solid, lotion or semisolid form for hand wash, face wash, body wash, or shaving applications; toothpaste/dentifrices for oral care applications or products for hard surface cleaning in bars or liquids form. If the product comprises an emulsion base, it preferably also comprises one or more surfactants as described below.

Surfactants

The antimicrobial composition according to the invention preferably comprises from 1 to 80% by weight of one or more surfactants. Surfactants may for instance advantageously contribute to the cleaning efficacy or the formulation stability of a composition.

Thus, the antimicrobial composition according to the invention preferably comprises
a. 0.001 to 5% by weight of the one or more monosubstituted phenols according to the invention,
b. 0.001 to 5% by weight of terpineol
c. a carrier, and
from 1 to 80% by weight of one or more surfactants.

It is particularly preferred that the antimicrobial composition comprises from 1 to 80% by weight of one or more surfactants in combination with the one or more monosubstituted phenols, and the terpineol at their more preferred concentrations as specified above.

In general, the surfactants may be chosen from the surfactants described in well-known textbooks like "Surface Active Agents" Vol. 1, by Schwartz & Perry, Interscience 1949, Vol. 2 by Schwartz. Perry & Berch, Interscience 1958, and/or the current edition of "McCutcheon's Emulsifiers and Detergents" published by Manufacturing Confectioners Company or in "Tenside-Taschenbuch", H. Stache, 2nd Edn., Carl Hauser Verlag, 1981; "Handbook of Industrial Surfactants" (4th Edn.) by Michael Ash and Irene Ash; Synapse Information Resources, 2008. Any type of surfactant, i.e. anionic, cationic, nonionic, zwitterionic or amphoteric can be used. Preferably, the one or more surfactants are anionic, nonionic, or a combination of anionic and nonionic surfactants. More preferably, the one or more surfactants are anionic.

A particularly preferred surfactant is soap. Soap is a suitable surfactant for personal washing applications of the antimicrobial composition of the invention. The soap is preferably $C_8$-$C_{24}$ soap, more preferably a $C_{10}$-$C_{20}$ soap and most preferably $C_{12}$-$C_{16}$ soap. The soap may or may not have one or more carbon-carbon double bonds or triple bonds. The cation of the soap can for instance be an alkali metal, alkaline earth metal or ammonium. Preferably, the cation of the soap is selected from sodium, potassium or ammonium. More preferably the cation of the soap is sodium or potassium.

The soap may be obtained by saponifying a fat and/or a fatty acid. The fats or oils may be fats or oils generally used in soap manufacture, such as tallow, tallow stearines, palm oil, palm stearines, soya bean oil, fish oil, castor oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soyabean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources. Other similar mixtures, such as those from palm oil and those derived from various animal tallow and lard are also included.

A typical fatty acid blend consists of 5 to 30%-wt coconut fatty acids and 70 to 95%-wt fatty acids ex hardened rice bran oil. Fatty acids derived from other suitable oils/fats such as groundnut, soybean, tallow, palm, palm kernel, etc. may also be used in other desired proportions. The soap, when present in solid forms of the present invention, is preferably present in an amount of 30 to 80%, more preferably from 50 to 80%, and even more preferably 55 to 75% by weight of the composition. The soap, when present in liquid forms of the composition is preferably present in 0.5 to 20%, more preferably from 1 to 10% by weight of the composition.

Other preferred surfactants fatty acid glycinates and fatty amphocarboxylates. These surfactants are particularly preferred in skin and hair cleaning compositions, because of their mild detergency and highly foaming nature. The fatty acid glycinates are salts of fatty acid amides of glycine, including for example sodium cocoyl glycinate. The fatty amphocarboxylates are amphoteric surfactants including for example sodium lauroamphoacetate (i.e. sodium 2-[1-(2-hydroxyethyl)-2-undecyl-4,5-dihydroimidazol-1-ium-1-yl] acetate). Yet another example of suitable surfactants are derivatives of isethionates, including acylisethionates.

The antimicrobial composition of the invention is also useful in hard surface cleaning applications. In such applications, preferred surfactants are nonionic surfactants, such as $C_8$-$C_{22}$, preferably $C_8$-$C_{16}$ fatty alcohol ethoxylates, comprising between 1 and 8 ethylene oxide groups when the product is in the liquid form. When the product for hard surface cleaning applications is in the solid form, surfactants are preferably selected from primary alkyl sulphates, secondary alkyl sulphonates, alkyl benzene sulphonates, ethoxylated alkyl sulphates, or alcohol ethoxylate nonionic surfactants. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16. Other classes of useful surfactants include cationic surfactants, such as long chain quaternary ammonium compounds and amphoteric surfactants such as betaines and alkyl dimethyl amine oxides. Suitable surfactant concentrations in liquid forms of hard surface cleaning application are generally from about from 0.5 to 10%, preferably from 1 to 5% by weight of the composition. In solid compositions, surfactant is preferably present in 5 to 40%, preferably from 10 to 30% by weight of the composition.

The antimicrobial composition of the invention is useful in oral care compositions e.g. in a dentifrice/toothpaste or an oral rinse product. In such applications, preferred surfactants are anionic, nonionic or amphoteric in nature, preferably anionic or amphoteric. The anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear $C_{10}$-$C_{18}$ chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Thus, it is highly preferred that the antimicrobial compositions include soap, alkyl sulphate or linear alkyl benzene sulphonate as the surfactants. More preferably, the one or more surfactants are selected from the group consisting of soaps, alkyl sulphates and linear alkyl benzene sulphonates.

Liquid and Solid Compositions

The antimicrobial composition may be in form of a solid, a liquid, a gel or a paste. A person skilled in the art can prepare compositions in various formats by choosing one or more carrier materials and/or surfactant. The antimicrobial compositions of the present invention are useful for cleansing and care, in particular for skin cleansing and skin care. It is envisaged that the antimicrobial composition can be used as a leave-on product or a wash-off product, preferably a wash-off product. The antimicrobial composition of the present invention can also be used for cleansing and care of hard surfaces such as glass, metal, plastic and the like.

A particularly preferred carrier is water. When water is present, it is preferably present in at least 1%, more preferably at least 2%, further more preferably at least 5% by weight of the composition. When water is the carrier, both liquid and solid compositions are possible. Different amounts of water may be preferred depending on the product format. When water is the carrier, a preferred liquid antimicrobial composition according to the invention comprises:
  a. 0.01 to 5% by weight of the one or more monosubstituted phenols,
  b. 0.05 to 5% by weight of the terpineol
  c. 10 to 99.9% by weight of water, and;
  d. 1 to 30% by weight of surfactant.

The liquid antimicrobial composition is useful for skin cleansing, in particular for hand wash or a face wash.

When water is the carrier, a preferred solid antimicrobial composition according to the invention comprises:
  a. 0.05 to 5% by weight of the one or more monosubstituted phenols.
  b. 0.05 to 5% by weight of the terpineol,
  c. 5 to 30% by weight of water, and;
  d. 30 to 80% by weight of surfactant.

The solid antimicrobial composition is preferably in form of a shaped solid, more preferably a bar. The solid antimicrobial composition is particularly useful for skin cleansing in particular for hand wash or a face wash.

Such a bar-shaped solid antimicrobial composition may for instance be a soap bar. Soap bar compositions are well-known and may be similar to the following non-limiting example composition, comprising 75.6 wt-% of anhydrous sodium soap, 1.0 wt-% of glycerine, 0.5 wt-% of sodium carbonate, 0.2 wt-% of EHDP (ethane-1-hydroxy-1,1-disphosphonate) acid, 0.04 wt-% of EDTA (ethylenediaminetetraacetic acid) tetrasodium salt, 8.5 wt-% of hydrated magnesium silicate (Talc), 0.7 wt-% of sodium chloride, 0.05 wt-% of dyes, 0.75 wt-% perfume, 0.05 to 10 wt-% of antimicrobial agents Including the monosubstituted phenols and the terpineol according to the present invention, and water up to 100 wt-%.

Alternatively, inorganic particulate material is also a suitable carrier. When inorganic particulate material is the carrier, the antimicrobial composition is in a solid form. Preferably the inorganic particulate material is talc. When the inorganic particulate material is talc, the solid antimicrobial composition is particularly useful as a talcum powder for application on face or body.

According to another alternative, a solvent different from water is a preferred carrier. Although any solvent can be used, alcohol is a preferred solvent. Short chain alcohols—in particular ethanol, propanol, and isopropanol—are particularly preferred as carrier for an antimicrobial wipe or an antimicrobial hand sanitiser composition.

Solvents like ethanol and isopropanol generally show antimicrobial efficacy themselves. However, they are also volatile and may readily evaporate during application of the composition. Thus, their levels on the surface that is treated might even reduce until below the minimum level required for antimicrobial action, before the minimum period needed for disinfection has passed. In contrast, the terpineol and the monosubstituted phenols according to the present invention are much less volatile and may therefore yield prolonged antimicrobial action after applying them to the skin.

Additional Ingredients

The composition may further comprise various additional ingredients known to a person skilled in the art. Such additional ingredients include but are not limited to: perfumes, pigments, preservative, emollients, sunscreens, emulsifiers, gelling agents, thickening agents, humectants (e.g. glycerine, sorbitol), sequestrants (e.g. EDTA) or polymers (e.g. cellulose derivatives for structuring such as methyl cellulose)

Both terpineol and some of the monosubstituted phenols according to the invention may contribute to the olfactory properties of the composition. Although some of these compounds might be applied for instance in perfume compositions, the present invention is directed towards antimicrobial compositions. Therefore, the composition is preferably not a perfume composition, although other perfume components can be present. Here, a perfume composition is defined as a composition comprising a plurality of olfactory components, wherein the composition is solely intended to provide a harmonious scent.

Synergistic Effect of the Invention

The inventors have surprisingly found that while one or more of the monosubstituted phenols according to the present invention alone or terpineol alone do not individually provide the fast antimicrobial kinetic action, a combination of one or more monosubstituted phenols and terpineol at the selective concentrations provides a synergistic antimicrobial action which is especially important in a wash off processes where the contact time of the antimicrobial actives with the surface is low, i.e. of the order of less than 5 minutes, preferably less than 2 minutes, further more preferably less than a minute and in many cases less than 15 seconds.

Synergistic Combinations of Monosubstituted Phenols and Terpineol

The antimicrobial action of two or more active compounds is considered additive if the combined action merely results from the addition of the effects the individual components would have in isolation. In contrast, the antimicrobial action of two or more active compounds is considered to be synergistic if the combined effect of the two or more compounds is stronger than expected based on the assumption of additivity. Without wishing to be bound by theory, it is believed that the antimicrobial action of the one compound is enhanced by the action of the other compound and vice versa. Such enhancement may for Instance originate from cooperative interplay between the mechanisms of antimicrobial action at the molecular level. Such enhanced antimicrobial action can manifest itself for instance by the fact that lower concentrations of active compounds are required to obtain complete microbial kill, or alternatively, that the same extent of microbial kill is arrived at in a shorter time.

Whether an antimicrobial composition comprising two or more active compounds is capable of synergistic antimicrobial action can for instance be determined following the procedures and using the criteria as outlined in Example 1 below. Typically, evidence of synergistic antimicrobial action is provided at concentrations below the minimum biocidal concentrations of each of the components when taken individually. However, it is generally believed that synergistic action can still occur when the concentration of one or more of the active compounds is raised above its minimum biocidal concentration (when taken individually).

The antimicrobial composition according to the present Invention preferably comprises the one or more monosubstituted phenols and terpineol according to the invention at concentrations at which they are capable of synergistic antimicrobial action. Thus, the concentrations of the one or more monosubstituted phenols and of the terpineol in the antimicrobial composition are preferably such that, when the composition is diluted or dissolved with a suitable medium during use, (e.g. when washing hands with water and a composition according to the invention) the concentration in the diluted or dissolved mixture is still sufficient to be antimicrobially efficacious. That is, to be capable of synergistic antimicrobial action, the concentrations of the one or more monosubstituted phenols and the terpineol in the composition ($C_{comp, phenol}$, and $C_{comp, terp}$, respectively) are preferably such that upon application, at a given concentration of the one or more monosubstituted phenols in the application medium ($C_{med, phenol}$), the terpineol is available at at least a minimum medium concentration ($C_{med, terp}$) or vice versa (i.e. such that at a given $C_{med, terp}$, a minimum $C_{med, phenol}$ is available, sufficient to provided synergistic antimicrobial action). Here, the application medium denotes the medium in which the antimicrobial action desirably takes place. For example, in personal care applications like hand-washing, the composition can be a solid soap bar. In that case, $C_{comp}$ refers to the concentration of the component in the soap bar, whereas $C_{med}$ refers to the concentration in the lather. The minimum and optimum concentrations can for instance be determined by a protocol as described for Example 1 or by one of the standards as detailed below. It is generally preferred that the concentrations of the one or more monosubstituted phenols and the terpineol in the composition according to the invention are equal to or higher than the optimal concentrations in the application medium, because in many typical applications, the composition is either used pure or is diluted to form the application medium.

Surprisingly, the synergy between the monosubstituted phenols and terpineol in compositions according to the invention, occurs over a wide range of concentrations and concentration ratios. Depending on factors including the type of antimicrobial composition, its intended application (for instance a hard surface cleaner, a skin cleanser, or a hand sanitiser) different concentration ranges and ratios will be preferred.

Thus, when for instance antimicrobial action against *E. Coli* is desired, the data of Example 1 can be used to determine preferable medium concentrations $C_{med}$. For example, in case complete microbial inactivation is desired in the particular medium of Example 1 and if the monosubstituted phenols is 2-tert-butylphenol, and $C_{med, phenol}$ is selected as 0.025% (w/v), $C_{med, terp}$ preferably is at least 0.15% (w/v) and vice versa.

Alternatively, the desired antimicrobial effect may be obtained by selecting a ratio of the respective concentrations of the one or more monosubstituted phenols and the terpineol. In view of the above-described considerations regarding the intended antimicrobial efficacy and other considerations, including for instance sensory properties, solubility, economic considerations, a concentration ratio of monosubstituted phenols to terpineol larger than one is preferred in some applications, whereas a concentration ratio of monosubstituted phenols to terpineol smaller than one is preferred in others, whereby the concentrations are expressed in %-wt.

Thus, in case a concentration ratio of monosubstituted phenols to terpineol smaller than one is desired, then the antimicrobial composition according to the invention preferably comprises the one or more monosubstituted phenols and the terpineol in a concentration ratio (monosubstituted phenols:monosubstituted phenols) of between 1:2 and 1:12, wherein the concentration is expressed as weight percent.

Alternatively, in case a concentration ratio of monosubstituted phenols to terpineol larger than one is desired, then the antimicrobial composition according to the invention preferably comprises the one or more monosubstituted phenols and terpineol in an applicable concentration ratio as specified hereinbelow.

For a number of preferred monosubstituted phenols, the following weight ratios are preferred.

In a preferred embodiment of the invention, the synergistic antimicrobial composition comprises (E)-2-(prop-1-enyl)phenol and terpineol. Preferably, a weight ratio of (E)-2-(prop-1-enyl)phenol to terpineol is from 1/0.13 to 1/1.5.

In a preferred embodiment of the invention, the synergistic antimicrobial composition comprises 4-propylphenol and terpineol. Preferably, a weight ratio of 4-propylphenol to terpineol is from 1/0.38 to 1/3.

In a preferred embodiment of the invention, the synergistic antimicrobial composition comprises 2-tert-butylphenol and terpineol. Preferably, a weight ratio of 2-tert-butylphenol to terpineol is about 1/3.75.

In a preferred embodiment of the invention, the synergistic antimicrobial composition comprises 2-sec-butylphenol and terpineol. Preferably, a weight ratio of 2-sec-butylphenol to terpineol is about 1/3.75.

In a preferred embodiment of the Invention, the synergistic antimicrobial composition comprises 3-n-propylphenol and terpineol. Preferably, a weight ratio of 3-n-propylphenol to terpineol is from 1/0.19 to 1/3.75, preferably from 1/0.33 to 1/3.75.

In a preferred embodiment of the invention, the synergistic antimicrobial composition comprises 4-n-butylphenol and terpineol. Preferably, a weight ratio of 4-n-butylphenol to terpineol is from 1/0.5 to 1/7.5.

In a preferred embodiment of the invention, the synergistic antimicrobial composition comprises 4-pentylphenol and terpineol. Preferably, a weight ratio of 4-pentylphenol to terpineol is from 1/0.17 to 1/3.

In a preferred embodiment of the invention, the synergistic antimicrobial composition comprises 4-sec-butylphenol and terpineol. Preferably, a weight ratio of 4-sec-butylphenol to terpineol is from 1/1 to 1/5.

In a preferred embodiment of the invention, the synergistic antimicrobial composition comprises 3-tert-butylphenol and terpineol. Preferably, a weight ratio of 3-tert-butylphenol to terpineol is from 1/3 to 1/3.75.

In a preferred embodiment of the invention, the synergistic antimicrobial composition comprises 2-hydroxydiphenylmethane and terpineol. Preferably, a weight ratio of 2-hydroxydiphenylmethane to terpineol is from 1/0.05 to 1/1.5, preferably from 1/0.19 to 1/1.5.

In a preferred embodiment of the invention, the synergistic antimicrobial composition comprises 4-hydroxydiphenylmethane and terpineol. Preferably, a weight ratio of 4-hydroxydiphenylmethane to terpineol is from 1/0.06 to 1/1.5, preferably from 1/0.06 to 1/0.13 or 1/0.33 to 1/1.5.

In a preferred embodiment of the invention, the synergistic antimicrobial composition comprises 2-cyclopentylphenol and terpineol. Preferably, a weight ratio of 2-cyclopentylphenol to terpineol is from 1/0.04 to 1/1, preferably from 1/0.04 to 1/0.15 or 1/0.2 to 1/1.

In a preferred embodiment of the invention, the synergistic antimicrobial composition comprises 4-cyclopentylphenol and terpineol. Preferably, a weight ratio of 4-cyclopentylphenol to terpineol is from 1/0.05 to 1/3, preferably from 1/0.19 to 1/3.

A further additional advantage of the present invention is that it is observed that treatment of a surface with a composition according to the invention comprising one or more monosubstituted phenols and terpineol, surprisingly enables continued protection of the surface against growth of microbes for a substantial period of time thereafter.

Effect of Including Surfactant

Favourably, compositions suitable in wash-off processes as described above include a surfactant for the cleaning action. To the further surprise of the inventors, while the surfactant alone does not provide the fast antimicrobial kill at the concentration present in wash off processes, it provides for further improvement in extent of reduction in viable microbial counts on the surface in the short period of time when surfaces are washed with a composition comprising one or more monosubstituted phenols, terpineol and additionally surfactant. Thus, while surfactant is generally known to be responsible for washing off dirt and also antimicrobial actives used in the composition, in the present invention, it provides a highly useful additional benefit in that it enhances the reduction of viable microbial count in a composition comprising a combination of monosubstituted phenols and terpineol alone.

However, it was surprisingly found that certain surfactants may reduce the activity of antimicrobial agents according to the invention. This happens for instance with cocoyl glycinate and lauroamphoacetate. Generally, surfactants are required in cleaning compositions to obtain good cleaning results. Since it is inter alia an object of this invention to provide antimicrobial cleaning compositions, it therefore also is an object of this invention to provide monosubstituted phenols capable of enhanced antimicrobial action upon combination with terpineol in the presence of such surfactants. It was found that in particular 2-n-propylphenol, 3-n-propylphenol, 4-n-propylphenol. 4-n-butylphenol, 2-tert-butylphenol, 3-tert-butylphenol, 4-tert-butylphenol, 2-sec-butylphenol, 4-sec-butylphenol, 3-phenylphenol, 2-benzylphenol, 4-benzylphenol, 2-cyclopentylphenol, (E-2-(prop-1-enyl)phenol show enhanced antimicrobial action in combination with terpineol. Therefore the composition according to the invention preferably comprises one or more monosubstituted phenols selected from the group consisting of 2-n-propylphenol, 3-n-propylphenol, 4-n-propylphenol. 4-n-butylphenol, 2-tert-butylphenol. 3-tert-butylphenol. 4-tert-butylphenol, 2-sec-butylphenol, 4-sec-butylphenol, 3-phenylphenol, 2-benzylphenol, 4-benzylphenol, 2-cyclopentylphenol, and (E)-2-(prop-1-enyl)phenol. More specifically, it is preferred that in case the composition according to the invention comprises a surfactant selected from cocoyl glycinate and lauroamphoacetate, that the monosubstituted phenol is selected from the group consisting of 2-n-propylphenol, 3-n-propylphenol, 4-n-propylphenol, 4-n-butylphenol, 2-tert-butylphenol, 3-tert-butylphenol, 4-tert-butylphenol, 2-sec-butylphenol, 4-sec-butylphenol. 3-phenylphenol, 2-benzylphenol 4-benzylphenol, 2-cyclopentylphenol, and (E)-2-(prop-1-enyl)phenol.

Method According to the Invention

According to the second aspect, the invention relates to a method of disinfecting a surface comprising the steps of
a. applying a composition according to the invention on to the surface; and
b. removing the composition from the surface.

Preferably, the surface is skin. Thus, for example, a surface like the hands, face, body, or the oral cavity is contacted with the composition of the invention. If the surface is a surface of a human or animal body, the method preferably is a non-therapeutic method of disinfecting a surface. Alternatively, the surface is any hard surface. Typically, such hard surfaces are surfaces that commonly require cleaning and preferably also require sanitisation or disinfection. Such surfaces may be found in many household or industrial environments, and may include for example kitchen and bathroom surfaces, table tops, floors, walls, windows, utensils, cutlery, and crockery. Such surfaces may be made from many different materials, including for instance plastics, wood, metal, ceramics, glass, concrete, marble, and painted surfaces.

The composition may be applied to the surface by any suitable means known to the skilled person. For instance, a suitable means may be pouring, dropping, spraying or wiping in case of liquid compositions.

Preferably, the method includes diluting or dissolving the composition with a suitable solvent, preferably water, before or whilst applying the composition to the surface. Such dissolving is preferred in particular in case the composition is a solid composition. Alternatively, solid compositions may also be directly spread, rubbed, or sprayed, e.g. in the form of a powder.

The method according to the first aspect of the present invention also includes the step of removing the composition from the surface. Here, removing the composition also encompasses partially removing the composition, because traces of the composition may remain on the surface. In many typical situations, such as washing of the skin or hard-surface cleaning, it is acceptable or sometimes even desirable if part of the composition—in particular certain active ingredients—remains on the surface. Therefore, step b preferably involves removing at least 5%, more preferably at least 10%, even more preferably at least 25%, still more preferably at least 50% and yet more preferably at least 75% of the composition by weight. Preferably, the step of removing the composition comprises rinsing the surface with a suitable solvent or wiping the surface with a suitable wipe, more preferably, this step consists of rinsing the surface with a suitable solvent or wiping the surface with a suitable wipe. Alternatively, the removal step can also include evaporation of part of the composition, for example when the composition comprises volatile components, e.g. solvents.

A suitable medium for rinsing the surface is water but it could also be for example a mixture of water and alcohol. It is then rinsed preferably with sufficient amounts of water after a pre-determined period of time to remove any visible or sensory residue of the composition. Alternatively, an alcohol wipe or a water/alcohol impregnated wipe may be used to wipe the surface to be visibly free of the antimicrobial composition. The step of removing the composition (e.g. by rinsing or wiping the surface) is preferably started less than 5 minutes, more preferably less than 2 minutes, even more preferably less than 1 minute, still more preferably less than 30 seconds and yet more preferably less than 20 seconds after commencement of the step of applying the composition on the surface, because of the surprisingly fast antimicrobial action of the compositions according to the present invention. Even though partial microbial kill may be almost instantaneous upon application of the composition according to the invention, it is preferred that the step of removing the composition from the surface is started out at least 5 seconds, preferably at least 10 seconds, more preferably at least 15 seconds after commencement of the step of applying the composition on the surface, in order to effect optimal antimicrobial action. Combinations of these times into time intervals are preferred too. Therefore, it is particularly preferred that the step of removing the composition from the surface (i.e. step b) is started between 2 minutes and 5 seconds, more preferably between 1 minute and 10 seconds, even more preferably between 30 and 10 seconds and still more preferably between 20 and 15 seconds after commencement of the step of applying the composition on the surface (i.e. step a).

Disinfection Time

These times between applying the composition and rinsing or wiping are preferably related to the disinfection time, in order to ensure optimal cleansing and sanitising of the surface. Therefore, the invention preferably relates to a method, wherein the disinfection time T of said method is less than 300 seconds, preferably less than 60 seconds, and more preferably less than 15 seconds; wherein T is defined as the time that elapses from the moment of adding the composition to a microbial culture until the number of microbes per unit volume of the culture is reduced by a factor of 100 000; and wherein the initial number of microbes preferably exceeds about 100 000 000 microbes per milliliter and wherein the composition is preferably a liquid composition.

The disinfecting action of the method (as may be expressed in terms of the disinfection time T) is preferably determined according to the protocol of Example 1 as described hereinafter. This test relates to a standardised test environment in which the microbial culture is kept in suspension. A similarly suitable test Is the standard suspension method described in European Standard EN1276, with the proviso that the disinfection time is adapted to suit the above criteria as will be clear to a person skilled in the art. Alternatively, one of the test methods as described in WO 2010/046238 may for instance be applied to establish the disinfecting action.

Such test methods may preferably also be used by the skilled person to determine the optimal concentrations of the one or more monosubstituted phenols and the terpineol in an antimicrobial composition according to the present invention.

Alternatively, since the method is directed towards surface disinfection, the disinfection time may also be determined by test methods involving a surface. Therefore, the invention preferably relates to a method according to the present invention, wherein the surface disinfection time T2 of said method is less than 60 seconds, preferably less than 15 seconds, wherein T2 is defined as the time starting from the moment of applying the composition to the surface to be disinfected after which the number of microbes per unit area is reduced by a factor of 10000 (i.e. a 4 log reduction), wherein the initial number of microbes preferably exceeds $10^3$, more preferably $10^5$, and even more preferably $10^7$ microbes per square centimeter. Such tests may for instance be performed as described in WO 20101046238, or as described in European Standards EN 13697:2001 and EN 1500:1997.

Use According to the Invention

The invention preferably provides for non-therapeutic benefits. Thus, for instance, the invention relates to use of an antimicrobial composition according to the present invention for faster reduction in viable microbial count.

Thus, according to the third aspect of the invention, there is provided use of a composition according to the invention for improved hygiene. Such use relates for example to use of an antimicrobial composition comprising the one or more monosubstituted phenols, terpineol and a carrier, for reduction in viable microbial count, preferably fast reduction of viable microbial count. Thus, such use preferably is use in a method for disinfection. Fast reduction in viable microbial count therefore preferably relates to use for disinfection whereby the disinfection time is less than 300 seconds, preferably less than 60 seconds, and more preferably less than 15 seconds. Here, the disinfection is preferably defined similar to the disinfection times T and T2 as described above.

Thus, there is provided use of a composition according to the invention for improved hygiene of surfaces of the human body. Such surfaces Include e.g. skin, hands and the oral cavity. According to a preferred aspect, the invention relates to use of a composition according to the invention for improved hand hygiene. According to another preferred aspect, the invention relates to use of a composition according to the invention for improved oral hygiene.

The microbicide compositions of the present invention can be used to inhibit the growth of microorganisms by introducing a microbicidally effective amount of the compositions onto, into or at a locus subject to attack. For instance, in the field of institutional and industrial applications, suitable loci include, for example: industrial process water Including electrocoat deposition systems, cooling towers and air washers; gas scrubbers; wastewater treatment; ornamental fountains; reverse osmosis filtration; ultrafiltration; ballast water; evaporative condensers and heat exchangers: pulp and paper processing fluids and additives; mineral slurries; starch; plastics; emulsions; dispersions: paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household and institutional products used in restaurants, healthcare facilities, schools, food processing facilities and farms including, cleaners, sanitizers and disinfectants, wipes, soaps, detergents, floor polishes and laundry rinse water; cosmetics; toiletries; shampoos; metalworking fluids; conveyor lubricants; hydraulic fluids; leather and leather processing products; textiles; textile and textile processing products; wood and wood processing products, such as plywood, chipboard, wallboard, flakeboard, laminated beams, oriented strandboard, hardboard, and particleboard; oil and gas processing fluids such as injection fluids, fracture fluids, drilling muds and produced water; fuel transportation and storage systems: agriculture adjuvant preservation; surfactant preservation: medical devices; diagnostic reagent preservation; food preservation, such as plastic or paper food wrap; food, beverage, and industrial process pasteurizers; toilet bowls; recreational water; pools; and spas.

Preferably, the microbicidal compositions of the present invention are used to inhibit the growth of microorganisms at a locus selected from one or more of mineral slurries, pulp and paper processing fluids and additives, starch, emulsions, dispersions, paints, latices, coatings, construction adhesives (such as ceramic adhesives), carpet backing adhesives, photographic chemicals, printing fluids, household and institutional products such as cleaners, sanitizers, disinfectants, wipes, cosmetics, toiletries, shampoos, soaps, detergents, floor polishes, laundry rinse water, metal working fluids, textile products, wood and wood products, agriculture adjuvant preservation, surfactant preservation, diagnostic reagent preservation, food preservation, food, beverage, and industrial process pasteurizers and oil and gas processing fluids.

Fields of Use

The composition according to the invention can in view of the above be applied for disinfection, reduction in viable microbial count or improved hygiene, especially at a surface. In preferred embodiments, the composition is particularly suited for application to the skin. For example, a surface like the hands, face, body, or the oral cavity can suitably be contacted with the composition of the invention. In other preferred embodiments, the surface is any hard surface. Typically, such hard surfaces are surfaces that commonly require cleaning and often also require sanitisation or disinfection. Such surfaces can be found in many household or industrial environments, and can include for example kitchen and bathroom surfaces, table tops, floors, walls, windows, utensils, cutlery, and crockery. Such surfaces can be made from many different materials, for instance plastics, wood, metal, ceramics, glass, concrete, marble, and painted surfaces. In other preferred embodiments, the compositions can be used for such disinfection, reduction in viable microbial count or improved hygiene at loci other than the surfaces as described hereinbefore.

In preferred embodiments, the invention relates to compositions according to the invention for use as or incorporation in home care products and personal care products. More preferably, this embodiment of the invention relates to a composition according to the invention which is a home care product or a personal care product.

A "home care product" is a product for the treatment, cleaning, caring or conditioning of the home or any of its contents. The foregoing includes, but is not limited to, compositions, products, or combinations thereof relating to or having use or application in the treatment, cleaning, cleansing, caring or conditioning of surfaces, furniture and atmosphere of the home and household contents, such as clothes, fabrics and/or cloth fibres and the manufacture of all of the foregoing products. A "personal care product" is a product for the treatment, cleaning, caring or conditioning of the person. The foregoing includes, but is not limited to, chemicals, compositions, products, or combinations thereof relating to or having use or application in the treatment, cleaning, cleansing or conditioning of the person (including in particular the skin, hair and oral cavity), and the manufacture of all the foregoing. Home care products and personal care products are for example products marketed under mass market brands, non-limiting examples being soap bars, deodorants, shampoos, and home surface sanitisers/disinfectants.

Another preferred embodiment of the invention relates to compositions according to the invention for use as or incorporation in industrial and/or institutional products. More preferably, this embodiment of the invention relates to a composition according to the invention which is an industrial and/or an institutional product. Industrial and institutional products are for example products being marketed under professional brands, non-limiting examples being for industrial, institutional, janitorial, and medical cleaning, cleaning-in-place, food services, veterinary, and agricultural products. Industrial and/or institutional products also include products for cleaning of the person (such as hand sanitisers) for medical offices, hospitals and/or other institutions.

In another preferred embodiment, the invention also relates to a method or use according to the invention involving home care products or personal care products. For example, the method according to the invention—which comprises application of a composition according to the Invention in step a—can be a method wherein that composition is a composition for use as or incorporation in home care products and personal care products as described hereinabove. Similarly, in another preferred embodiment, the invention also relates to a method or use according to the invention involving industrial and/or institutional products. For example, the method according to the invention—which comprises application of a composition according to the invention in step a—can be a method wherein that composition is a composition for use as or incorporation in industrial and/or institutional products as described hereinabove.

Products and/or methods for use in the home care or personal care field are generally distinct from products and/or methods for use in the industrial and/or institutional field. Thus, for example, a product that is marketed as a home or personal care product will generally not be marketed as a product for industrial and/or institutional use and vice versa. Therefore, certain embodiments of the present invention, when carried forth into practice, will relate to the one field, but not the other.

EXAMPLES

The invention is illustrated by the following non-limiting examples.

Example 1

Assessment of Antimicrobial Efficacy

Materials

Monosubstituted phenols were purchased as fine chemicals from suppliers such as Sigma Aldrich, Alfa Aesar and TCI Fine Chemicals.

A terpineol mixture comprising ca 88 wt-% of (S)-alpha-terpineol, and 12 wt-% of gamma-terpineol was purchased from Sigma Aldrich and used throughout the examples (being referred to as alpha-terpineol or terpineol) unless specified otherwise.

General Method for Assessment of Antimicrobial Synergy

The efficacies of antimicrobial agents can be usefully compared by determining the Minimum Biocidal Concentration (MBC). The MBC is defined as the lowest absolute concentration of the particular active that provides complete kill (zero bacterial growth). The differing behaviours of inhibitory antimicrobtals in Isolation and mixtures have been widely explored using the concept of the Fractional Concentration and Fractional Inhibitory Concentration (FIC). See for instance J R W Lambert and R Lambert, *J. Appl. Microblol* 95, 734 (2003); T. Jadavji. C G Prober and R Cheung. *Antimicrobial Agents and Chemotherapy* 26, 91 (1984), and WO 2004/006876. These parameters can be defined as follows:

$$FC(\text{component } a) = \frac{\text{Concentration of component } a \text{ tested in the mixture}}{\text{MIC(component } a \text{ tested as a single active)}}$$

$$FIC(\text{component } a) = \frac{\text{MIC(component } a \text{ tested in the mixture)}}{\text{MIC(component } a \text{ tested as a single active)}}$$

By analogy the Fractional Biocidal Concentration (FBC) is given by:

$$FBC(\text{component } a) = \frac{\text{MBC(component } a \text{ tested in the mixture)}}{\text{MBC(component } a \text{ tested as a single active)}}$$

The interactions between antimicrobials can be additive, synergistic or possibly antagonistic depending on whether the efficacy of the combination is equivalent to, greater than or less than that obtained for the same total concentration of the individual components when tested alone.

These relationships can be expressed mathematically by summing the fractional MBC values for all the components present in the mixture to give the "fractional biocidal index":

$$\Sigma FBC = FBC_{(component\ 1)} + FBC_{(component\ 2)} + FBC_{(component\ 3)} + \ldots \text{etc}$$

such that
  $\Sigma FBC \geq 1$ corresponds to additive or antagonistic bactericidal activity
  $\Sigma FBC < 1$ corresponds to synergistic bactericidal activity Experimental Method Antimicrobial efficacy is tested against a representative pathogenic bacterial organism, Gram negative *Escherichia coli*. Concentrations of actives are expressed in terms of the percentage weight/volume (% w/v) throughout Example 1.
Bacterial Stock An overnight culture of *Escherichia coli* (10536 strain) was prepared in 50 ml total volume of TSB broth, grown for ca. 18 hrs at 37° C. and shaken at 150 rpm. 1 ml of this overnight *E. coli* culture was transferred to 50 ml of fresh TSB broth and incubated at 37° C. at 150 rpm for ca. 4 hours. This culture was separated into equal volumes and centrifuged at 4000 rpm for 15 minutes, washed with sterile saline (0.85% NaCl), centrifuged once more and re-suspended in saline to give a final concentration of 0.8 $OD_{620}$ equivalent to about $10^8$ cells per milliliter for this particular organism. Here, $OD_{620}$ indicates the absorbance of a sample in a cuvette of 1.0 cm path length at a wavelength of 620 nm. This bacterial stock was used for assaying against antimicrobial actives (in triplicate).
Protocol The following assay describes the testing of 8 materials using 6 dilutions across half of a 96-well micro titre plate (MTP). Using this approach it is possible to assay 16 actives (without replicates) with one full dilution plate, replicating this set up in two halves of the plate columns, 1-6 and 7-12.

1M solutions of the test actives were prepared in dimethylsulphoxide (DMSO). Stock solutions of the actives at 1.11 times the desired final concentration were prepared by diluting the DMSO solutions in water, so that for example a 0.89% w/v solution was prepared for a desired "in test" concentration of 0.8% w/v in order to allow for the further dilution of the active when the bacterial suspension is added (dilution from 270 µl to 300 µl), as described below.

Aliquots (270 μl) of the materials at 1.11 times the final concentration were dispensed into the wells of the MTP along one column (A1-H1). This MTP was labelled as the "Screening plate".

In another MTP, labelled as the "Dilution plate", 270 μl of D/E neutralising solution from DIFCO Composition was added to column 1. The composition of the neutralising solution was as follows: pancreatic digest of casein, 5.0 g/L; Yeast Extract, 2.5 g/L; Dextrose, 10 g/L, sodium thioglycollate, 1.0 g/L; sodium thiosulphate, 6.0 g/L; sodium bisulphite, 2.5 g/L; Polysorbate 80, 5.0 g/L; lecithin 7.0 g/L; bromocresol purple, 0.02 g/L with a pH in the range 7.6±0.2.

270 μl of tryptone diluent solution was added to all the remaining wells of the Dilution MTP (columns 2-6).

Bacterial stock (30 μl) was then added to the prepared 270 μl of the solution of actives in the Screening Plate and mixed, using a multichannel pipette with 8 tips to aspirate and dispense the same volume of bacterial stock in parallel to 8 wells in rows A-H. After a contact time of 15 seconds, the mixtures were quenched by transferring 30 μl volumes of the mixtures into the 270 μl D/E neutralising solution in the prepared dilution plate, using aspiration to mix. After exactly 5 minutes in the DIE neutralising solution, 30 μl volumes were transferred from column 1 to column 2 of the Dilution MTP and mixed, before transferring further 30 μl volumes from column 2 into column 3. This process was repeated serially diluting the bacteria across the plate to column 6.

30 μl volumes from each well in the Dilution MTP were transferred onto pre-labelled segment of Tryptone Soya Agar (TSA) plates starting from the lowest bacterial concentration (highest dilution, column 6) to the highest bacterial concentration (column 1). The TSA plates were allowed to stand for ca. 2 hours so that the 30 μl inocula spots could dry and the plates were then inverted and incubated overnight at 37° C. before enumerating the bacterial colonies at the labelled dilutions to determine the effects of the actives on bacterial growth.

Calculation of Results

Mean bacterial survival numbers $N_{MBS}$ (expressed in Log CFU/ml) are obtained by first determining the segment of the TSA plate where the number of bacterial colonies is countable. From the colony number in this segment. $N_{MBS}$ is calculated by the formula:

$$N_{MBS} = \log \{N_{col} \cdot 10^{DF} \cdot 100/3\}$$

Here, $N_{col}$ is the colony count, and DF is the dilution factor taken from the MTP-well corresponding to the TSA plate segment (i.e. DF may range from 1 for the quench, to 6 for the highest dilution). The factor 100/3 is a conversion factor from the volume of the inocula spot to one milliliter.

Every assay test was performed in triplicate. The reported mean bacterial survival results are the average of such a triplet, the error is the corresponding standard deviation.

Thus, a value of $N_{MBS}$ of about 7 corresponds to a count of about 3 colonies from the fifth dilution well, i.e. with DF=5. Such a count of about 7 is generally observed when bacteria are exposed to non-biocidal materials. In case no surviving colonies are observed in any segment of the TSA plate, this is interpreted as complete kill and a value of $N_{MBS}=0$ is reported.

Validation

All test results were validated by running every test assay in parallel with four control experiments on the same MTP. All control experiments are executed exactly according to the above protocol, but with the following active ingredients:

A 0.025% (w/v) thymol
B 0.15% (w/v) alpha-terpineol
C 0.025% (w/v) thymol+0.15% (w/v) alpha-terpineol
D no active component The control experiments A, B and D validate a test assay by not showing bacterial kill, whereas control experiment C, comprising a synergistic combination of thymol and alpha-terpineol according to WO 2010/046238 A1 validates a test assay by showing complete bacterial kill.

A reference experiment according to the above protocol, but without active component, showed that DMSO does not affect bacterial growth at the concentrations present in the test solutions in this protocol (<5% (w/v)), as can be seen in Table 4.

TABLE 4

| DMSO in water (% w/v) | Mean bacterial survival [log CFU/ml] | Standard deviation |
| --- | --- | --- |
| 4.5 | 8.2 | 0.1 |
| 3.6 | 8.4 | 0.2 |
| 2.7 | 8.2 | 0.1 |
| 1.8 | 8.5 | 0.2 |
| 0.9 | 8.6 | 0.1 |
| 0.0 | 8.5 | 0.1 |

Results

The above method was applied to asses the antibacterial efficacy of the monosubstituted phenols according to the invention. Table 5 shows the antibacterial activities of the monosubstituted phenols, both alone and in conjunction with terpineol.

TABLE 5

Antibacterial activities of thymol, and monosubstituted phenols alone and in combination with terpineol

| Example | Monosubstituted phenol concentration $C_{(phenol)}$ (% w/v) | Concentration of terpineol $C_{TERP}$ (% w/v) | $N_{MBS}$ [log CFU/ml] | Standard deviation |
| --- | --- | --- | --- | --- |
| 1:1* | 0.075% thymol | 0 | 0 | 0 |
| 1:2* | 0.05% thymol | 0 | 0 | 0 |
| 1:3* | 0.025% thymol | 0 | >7 | 0.1 |
| 1:4* | 0 | 0.5% alpha-terpineol | 0 | 0 |
| 1:5* | 0 | 0.4% alpha-terpineol | 0 | 0 |
| 1:6* | 0 | 0.3% alpha-terpineol | 7 | 0.2 |
| 1:7* | 0 | 0.15% alpha-terpineol | 7 | 0.2 |
| 1:8* | 0.075% 4-n-propylphenol | 0 | 0 | 0 |
| 1:9* | 0.0375% 4-n-propylphenol | 0 | 7.8 | 0.2 |
| 1:10 | 0.0375% 4-n-propylphenol | 0.15% alpha-terpineol | 0 | 0 |
| 1:11 | 0.025% 4-n-propylphenol | 0.15% alpha-terpineol | 0 | 0 |
| 1:12* | 0.025% 4-n-butylphenol | 0 | 0 | 0 |
| 1:13* | 0.0125% 4-butylphenol | 0 | 7.0 | 0.7 |
| 1:14 | 0.0125% 4-n-butylphenol | 0.15% alpha-terpineol | 0 | 0 |
| 1:15* | 0.025% 4-n-pentylphenol | 0 | 0 | 0 |
| 1:16* | 0.0125% 4-pentylphenol | 0 | 6.6 | 0.2 |

TABLE 5-continued

Antibacterial activities of thymol, and monosubstituted phenols alone and in combination with terpineol

| Example | Mono-substituted phenol concentration $C_{(phenol)}$(% w/v) | Concentration of terpineol $C_{TERP}$(% w/v) | $N_{MBS}$ [log CFU/ml] | Standard deviation |
|---|---|---|---|---|
| 1:17 | 0.0125% 4-pentylphenol | 0.15% alpha-terpineol | 0 | 0 |
| 1:18* | 0.05% 2-tert-butylphenol | 0 | 0 | 0 |
| 1:19* | 0.025% 2-tert-butylphenol | 0 | 7.5 | 0.1 |
| 1:20 | 0.025% 2-tert-butylphenol | 0.15% alpha-terpineol | 0 | 0 |
| 1:21* | 0.08% 3-tert-butylphenol | 0 | 0 | 0 |
| 1:22* | 0.05% 3-tert-butylphenol | 0 | 7.6 | 0.5 |
| 1:23 | 0.04% 3-tert-butylphenol | 0.15% alpha-terpineol | 0 | 0 |
| 1:24* | 0.05% 2-sec-butylphenol | 0 | 0 | 0 |
| 1:25* | 0.025% 2-sec-butylphenol | 0 | 7.5 | 0.1 |
| 1:26 | 0.025% 2-sec-butylphenol | 0.15% alpha-terpineol | 0 | 0 |
| 1:27* | 0.08% 4-sec-butylphenol | 0 | 0 | 0 |
| 1:28* | 0.05% 4-sec-butylphenol | 0 | 4.1 | 3.6 |
| 1:29* | 0.025% 4-sec-butylphenol | 0 | 7.6 | 0.2 |
| 1:30 | 0.025% 4-sec-butylphenol | 0.15% alpha-terpineol | 0 | 0 |
| 1:31* | 0.1% 2-cyclopentylphenol | 0 | 0 | 0 |
| 1:32* | 0.08% 2-cyclopentylphenol | 0 | 3.4 | 0.3 |
| 1:33* | 0.05% 2-cyclopentylphenol | 0 | 7.5 | 0.5 |
| 1:34 | 0.025% 2-cyclopentylphenol | 0.15% alpha-terpineol | 0 | 0 |
| 1:35* | 0.08% 4-cyclopentylphenol | 0 | 0 | 0 |
| 1:36* | 0.05% 4-cyclopentylphenol | 0 | 7.1 | 0.3 |
| 1:37 | 0.04% 4-cyclopentylphenol | 0.15% alpha-terpineol | 0 | 0 |
| 1:38* | 0.15%(E)-2-(prop-1-enyl)phenol | 0 | 0 | 0 |
| 1:39* | 0.075% (E)-2-(prop-1-enyl)phenol | 0 | 6.9 | 0.1 |
| 1:40 | 0.075% (E)-2-(prop-1-enyl)phenol | 0.15% alpha-terpineol | 0 | 0 |
| 1:41* | 0.05% 2-benzylphenol | 0 | 0 | 0 |
| 1:42* | 0.025% 2-benzylphenol | 0 | 7.1 | 0.3 |
| 1:43 | 0.025% 2-benzylphenol | 0.15% alpha-terpineol | 0 | 0 |
| 1:44* | 0.05% 4-benzylphenol | 0 | 0 | 0 |
| 1:45* | 0.025% 4-benzylphenol | 0 | 3.8 | 0.2 |
| 1:46 | 0.025% 4-benzylphenol | 0.15% alpha-terpineol | 0 | 0 |
| 1:47* | 0.075% 2-methylphenol | 0.15% alpha-terpineol | 8.1 | 0.4 |
| 1:48* | 0.025% 2-methylphenol | 0.15% alpha-terpineol | 7.9 | 0.4 |
| 1:49* | 0.025% 4-hexylphenol | 0.15% alpha-terpineol | 6.8 | 0.4 |
| 1:50* | 0.025% 4-heptylphenol | 0.15% alpha-terpineol | 8.1 | 0.5 |
| 1:51* | 0.025% eugenol (4-allyl-2-methoxy-phenol) | 0.15% alpha-terpineol | 7.8 | 0.2 |

*Examples marked with an asterisk (*) are comparative examples

Comparative Examples

Determination of the parameter ΣFBC, which is used as measure of the synergistic antimicrobial action of compositions according to the present invention, requires determination of the Minimum Biocidal Concentrations (MBCs) of the relevant actives first. As described above, the MBC for an active can be defined as the lowest concentration of the active that provides zero bacterial survival in the particular medium. Data for examples (1:1) to (1:3) demonstrate that the MBC value for thymol is 0.05% (w/v). For alpha-terpineol, compositions (1:4) to (1:7), show that the MBC is 0.4% w/v. The same analysis has been carried out for selected monosubstituted phenols and is summarised in Table 6 below. These MBC values constitute the upper boundaries to the respective MBCs in the particular medium used in these examples.

TABLE 6

Minimum biocidal concentrations of antimicrobial components

| Component | MBC (% w/v) |
|---|---|
| Thymol | 0.05 |
| alpha-terpineol | 0.4 |
| 4-n-propylphenol | 0.075 |
| 4-n-butylphenol | 0.025 |
| 4-pentylphenol | 0.025 |
| 2-tert-butylphenol | 0.05 |
| 3-tert-butylphenol | 0.08 |
| 2-sec-butylphenol | 0.05 |
| 4-sec-butylphenol | 0.08 |
| 2-cyclopentylphenol | 0.1 |
| 4-cyclopentylphenol | 0.08 |
| (E)-2-(prop-1-enyl)phenol | 0.15 |
| 2-benzylphenol | 0.05 |
| 4-benzylphenol | 0.05 |

It is clear from the data in Table 6 that the monosubstituted phenols according to the present invention are antimicrobially efficacious.

Synergistic Interactions

The tested combinations of the selected monosubstituted phenols with terpineol provide complete bacterial kill in the examples (1:10), (1:11), (1:14), (1:17), (1:20), (1:23), (1:26), (1:30), (1:34), (1:37), (1:40), (1:43), and (1:46). Using the MBC values listed in Table 6 above, the fractional MBC values for the components present in these mixtures and the experimental ΣFBC of the compositions can be calculated in order to discriminate between combinations providing evidence of synergistic effects, as opposed to additive biocidal effects. The results from this analysis are given in Table 7.

TABLE 7

Extent of synergistic interactions between binary compound mixtures for compositions providing complete bacterial kill

| compound | Ex. | monosubstituted phenol MBC % (w/v) | $FBC^a$ | terpineol MBC % (w/v) | $FBC^b$ | $\Sigma FBC$ | Evidence of Synergy$^c$ |
|---|---|---|---|---|---|---|---|
| 4-n-propylphenol | 1:10 | 0.075 | 0.5 | 0.4 | 0.38 | 0.88 | Yes |
| 4-n-propylphenol | 1:11 | 0.075 | 0.33 | 0.4 | 0.38 | 0.71 | Yes |
| 4-n-butylphenol | 1:14 | 0.025 | 0.5 | 0.4 | 0.38 | 0.88 | Yes |
| 4-n-pentylphenol | 1:17 | 0.025 | 0.5 | 0.4 | 0.38 | 0.88 | Yes |
| 2-tert-butylphenol | 1:20 | 0.05 | 0.5 | 0.4 | 0.38 | 0.88 | Yes |
| 3-tert-butylphenol | 1:23 | 0.08 | 0.5 | 0.4 | 0.38 | 0.88 | Yes |
| 2-sec-butylphenol | 1:26 | 0.05 | 0.5 | 0.4 | 0.38 | 0.88 | Yes |
| 4-sec-butylphenol | 1:30 | 0.08 | 0.31 | 0.4 | 0.38 | 0.69 | Yes |
| 2-cyclopentylphenol | 1:34 | 0.1 | 0.25 | 0.4 | 0.38 | 0.63 | Yes |
| 4-cyclopentylphenol | 1:37 | 0.08 | 0.5 | 0.4 | 0.38 | 0.88 | Yes |
| (E)-2-(prop-1-enyl)phenol | 1:40 | 0.15 | 0.5 | 0.4 | 0.38 | 0.88 | Yes |
| 2-benzylphenol | 1:43 | 0.05 | 0.5 | 0.4 | 0.38 | 0.88 | Yes |
| 4-benzylphenol | 1:46 | 0.05 | 0.5 | 0.4 | 0.38 | 0.88 | Yes |

$^a$FBC of phenol: $C_{phenol}/MBC_{phenol}$
$^b$FBC of terpineol: $C_{terpineol}/MBC_{terpineol}$
$^c$Criterion for synergy: ($\Sigma FBC < 1$)

For Examples for which the $\Sigma FBC$ value is below 1 in Table 7 provide evidence for synergistic interactions, according to the set criteria. Therefore, these examples show how the antimicrobial efficacy of terpineol and the monosubstituted phenols according to invention are enhanced when they are applied together. Such synergies allow for reductions in the concentrations of the antimicrobials required to achieve complete kill. For example 0.4% w/v terpineol is required to achieve complete bacterial kill when tested in isolation but this can be reduced 2.7-fold to 0.15% (w/v) when used in combination with 0.025% w/v of 2-tert-butylphenol or 0.025% w/v of 2-cyclopentylphenol.

Comparative Examples

The comparative examples (1:47) to (1:51) show that compositions comprising terpineol and phenolic compounds that are not compounds according to the present invention (2-methylphenol, 4-hexylphenol, 4-heptylphenol and eugenol) at concentrations comparable to those in the examples according to the invention do not give rise to fast antimicrobial action.

Example 2

In this Example, a wide range of combinations of chemicals was tested by conducting high resolution MBC assays of monosubstituted phenols in the presence of various concentrations of terpineol. The materials were sourced in the same way as for Example 1. Synergy tests were conducted using standard microtiter plate assays with phosphate buffer containing 35% dipropylene glycol (DPG). High resolution MBCs were determined by adding varying amounts of microbicide to one column of a microtiter plate and doing subsequent ten-fold dilutions using an automated liquid handling system to obtain a series of endpoints ranging from 0.002% to 1% of the test compound. The MBC plate was inoculated one column at a time with the test microorganism. An aliquot of the inoculated well was transferred at 15 seconds to a plate containing a neutralizing agent (D/E Neutralizing Broth), mixed and held for 5 minutes before being transferred to a growth plate containing trypticase soy broth (TSB). The TSB plate was incubated at 37° C. and read for the presence/absence of growth at 24 hours. The lowest level tested that provided complete kill (as evidenced by lack of growth on the microtitre plate) of the test organisms in 15 seconds is defined as the minimum biocidal concentration (MBC) throughout Example 2.

The synergy of the combinations of the present invention was determined against a the same bacterium as in Example 1, Escherichia coli (E. coli—ATCC #10536), at a concentration of approximately $1 \times 10^8$ bacteria per mL. This microorganism is representative of natural contaminants in many consumer and industrial applications. The plates were visually evaluated for microbial growth (turbidity) to determine the MBC after 24 hours incubation time at 37° C.

The test results for demonstration of synergy of the combinations of the present invention are shown below in the Tables 8 to 21. Each of these tables shows the specific combinations of two components; results against the microorganism tested; the end-point activity in weight % measured by the MBC for the first component alone (monosubstituted phenol, $MBC_A$), for the second component alone (terpineol, $MBC_B$), for the first component in the mixture ($C_a$) and for the second component in the mixture ($C_b$); the calculated $\Sigma FBC$ value; and the range of synergistic ratios for each combination tested (first component to second component or A/B) against the particular microorganism.

Data in the tables below include the range of ratios that were found to be synergistic. (Data which were collected outside of the synergistic ranges are not reported.) These data demonstrate that certain combinations of monosubstituted phenols according to the present invention and terpineol show more enhanced control over the microorganisms than would be expected if the combinations were additive rather than synergistic.

TABLE 8

First Component (A) = (E)-2-(prop-1-enyl)phenol
Second Component (B) = terpineol

| Microorganism | $C_a$ | $C_b$ | $\Sigma FBC$ | Ratio A to B |
|---|---|---|---|---|
| E. coli 10536 | 0.8 | 0 | 1.00 | |
| | 0.8 | 0.025 | 1.04 | 1 to 0.03 |
| | 0.8 | 0.05 | 1.08 | 1 to 0.06 |
| | 0.6 | 0.075 | 0.88 | 1 to 0.13 |
| | 0.6 | 0.1 | 0.92 | 1 to 0.17 |
| | 0.2 | 0.3 | 0.75 | 1 to 1.5 |
| | 0.3 | 0.3 | 0.88 | 1 to 1 |
| | 0 | 0.6 | 1.00 | |

The ratios of (E)-2-(prop-1-enyl)phenol to terpineol tested ranged from 1/0.025 to 1/400. The synergistic ratios of (E)-2-(prop-1-enyl)phenol to terpineol ranged from 1/0.13 to 1/1.5.

TABLE 9

First Component (A) = 4-propylphenol
Second Component (B) = terpineol

| Microorganism | $C_a$ | $C_b$ | ΣFBC | Ratio A to B |
|---|---|---|---|---|
| E. coli 10536 | 0.3 | 0 | 1.00 | |
| | 0.3 | 0.025 | 1.04 | 1 to 0.08 |
| | 0.3 | 0.05 | 1.08 | 1 to 0.17 |
| | 0.2 | 0.075 | 0.79 | 1 to 0.38 |
| | 0.3 | 0.1 | 1.17 | 1 to 0.33 |
| | 0.1 | 0.3 | 0.83 | 1 to 3 |
| | 0 | 0.6 | 1.00 | |

The ratios of 4-propylphenol to terpineol tested ranged from 1/0.025 to 1/400. The synergistic ratios of 4-propylphenol to terpineol range from 1/0.38 to 1/3.

TABLE 10

First Component (A) = 2-tert-butylphenol
Second Component (B) = terpineol

| Microorganism | $C_a$ | $C_b$ | ΣFBC | Ratio A to B |
|---|---|---|---|---|
| E. coli 10536 | 0.2 | 0 | 1.00 | |
| | 0.2 | 0.025 | 1.04 | 1 to 0.13 |
| | 0.2 | 0.05 | 1.08 | 1 to 0.25 |
| | 0.2 | 0.075 | 1.13 | 1 to 0.38 |
| | 0.2 | 0.1 | 1.17 | 1 to 0.5 |
| | 0.08 | 0.3 | 0.90 | 1 to 3.75 |
| | 0 | 0.6 | 1.00 | |

The ratios of 2-tert-butylphenol to terpineol tested ranged from 1/0.025 to 1/400. The synergistic ratio of 2-tert-butylphenol to terpineol is 1/3.75.

TABLE 11

First Component (A) = 2-sec-butylphenol
Second Component (B) = terpineol

| Microorganism | $C_a$ | $C_b$ | ΣFBC | Ratio A to B |
|---|---|---|---|---|
| E. coli 10536 | 0.2 | 0 | 1.00 | |
| | 0.2 | 0.025 | 1.04 | 1 to 0.13 |
| | 0.2 | 0.05 | 1.08 | 1 to 0.25 |
| | 0.2 | 0.075 | 1.13 | 1 to 0.38 |
| | 0.2 | 0.1 | 1.17 | 1 to 0.5 |
| | 0.08 | 0.3 | 0.90 | 1 to 3.75 |
| | 0 | 0.6 | 1.00 | |

The ratios of 2-sec-butylphenol to terpineol tested ranged from 1/0.025 to 1/400. The synergistic ratio of 2-sec-butylphenol to terpineol is 1/3.75.

TABLE 12

First Component (A) = 2-n-propylphenol
Second Component (B) = terpineol

| Microorganism | $C_a$ | $C_b$ | ΣFBC | Ratio A to B |
|---|---|---|---|---|
| E. coli 10536 | 0.3 | 0 | 1.00 | |
| | 0.6 | 0.025 | 2.04 | 1 to 0.04 |
| | 0.2 | 0.05 | 0.75 | 1 to 0.25 |
| | 0.3 | 0.075 | 1.13 | 1 to 0.25 |
| | 0.3 | 0.1 | 1.17 | 1 to 0.33 |
| | 0.1 | 0.3 | 0.83 | 1 to 3 |
| | 0 | 0.6 | 1.00 | |

The ratios of 2-n-propylphenol to terpineol tested ranged from 1/0.025 to 1/350. The synergistic ratios of 2-n-propylphenol to terpineol range from 1/0.25 to 1/3.

TABLE 13

First Component (A) = 3-n-propylphenol
Second Component (B) = terpineol

| Microorganism | $C_a$ | $C_b$ | ΣFBC | Ratio A to B |
|---|---|---|---|---|
| E. coli 10536 | 0.05 | 0 | 1.00 | |
| | 0.8 | 0.025 | 1.64 | 1 to 0.03 |
| | 0.5 | 0.05 | 1.08 | 1 to 0.10 |
| | 0.3 | 0.075 | 0.73 | 1 to 0.25 |
| | 0.4 | 0.075 | 0.93 | 1 to 0.19 |
| | 0.3 | 0.1 | 0.77 | 1 to 0.33 |
| | 0.4 | 0.1 | 0.97 | 1 to 0.25 |
| | 0.08 | 0.3 | 0.66 | 1 to 3.75 |
| | 0.1 | 0.3 | 0.70 | 1 to 3 |
| | 0.2 | 0.3 | 0.90 | 1 to 1.5 |
| | 0 | 0.6 | 1.00 | |

The ratios of 3-n-propylphenol to terpineol tested ranged from 1/0.025 to 1/400. The synergistic ratios of 3-n-propylphenol to terpineol range from 1/0.19 to 1/3.75.

TABLE 14

First Component (A) = 4-n-butylphenol
Second Component (B) = terpineol

| Microorganism | $C_a$ | $C_b$ | ΣFBC | Ratio A to B |
|---|---|---|---|---|
| E. coli 10536 | 0.2 | 0 | 1.00 | |
| | 0.2 | 0.025 | 1.04 | 1 to 0.13 |
| | 0.1 | 0.05 | 0.58 | 1 to 0.5 |
| | 0.1 | 0.075 | 0.63 | 1 to 0.75 |
| | 0.1 | 0.1 | 0.67 | 1 to 1 |
| | 0.04 | 0.3 | 0.70 | 1 to 7.5 |
| | 0.05 | 0.3 | 0.75 | 1 to 6 |
| | 0.06 | 0.3 | 0.80 | 1 to 5 |
| | 0.08 | 0.3 | 0.90 | 1 to 3.75 |
| | 0 | 0.6 | 1.00 | |

The ratios of 4-n-butylphenol to terpineol tested ranged from 1/0.025 to 1/400. The synergistic ratios of 4-n-butylphenol to terpineol range from 1/0.5 to 1/7.5.

TABLE 15

First Component (A) = 4-pentylphenol
Second Component (B) = terpineol

| Microorganism | $C_a$ | $C_b$ | ΣFBC | Ratio A to B |
|---|---|---|---|---|
| E. coli 10536 | 1.0 | 0 | 1.00 | |
| | 1 | 0.025 | 1.04 | 1 to 0.03 |
| | 2 | 0.05 | 2.08 | 1 to 0.03 |
| | 2 | 0.075 | 2.13 | 1 to 0.04 |
| | 0.4 | 0.1 | 0.57 | 1 to 0.25 |
| | 0.5 | 0.1 | 0.67 | 1 to 0.20 |
| | 0.6 | 0.1 | 0.77 | 1 to 0.17 |
| | 0.1 | 0.3 | 0.60 | 1 to 3 |
| | 0.2 | 0.3 | 0.70 | 1 to 1.5 |
| | 0 | 0.6 | | |

The ratios of 4-pentylphenol to terpineol tested ranged from 1/0.025 to 1/400. The synergistic ratios of 4-pentylphenol to terpineol range from 1/0.17 to 1/3.

TABLE 16

First Component (A) = 4-sec-butylphenol
Second Component (B) = terpineol

| Microorganism | $C_a$ | $C_b$ | ΣFBC | Ratio A to B |
|---|---|---|---|---|
| E. coli 10536 | 0.2 | 0 | 1.00 | |
| | 0.2 | 0.025 | 1.04 | 1 to 0.13 |

TABLE 16-continued

First Component (A) = 4-sec-butylphenol
Second Component (B) = terpineol

| Microorganism | $C_a$ | $C_b$ | ΣFBC | Ratio A to B |
|---|---|---|---|---|
|  | 0.2 | 0.05 | 1.08 | 1 to 0.25 |
|  | 0.2 | 0.075 | 1.13 | 1 to 0.38 |
|  | 0.1 | 0.1 | 0.67 | 1 to 1 |
|  | 0.06 | 0.3 | 0.80 | 1 to 5 |
|  | 0.08 | 0.3 | 0.90 | 1 to 3.75 |
|  | 0 | 0.6 | 1.00 |  |

The ratios of 4-sec-butylphenol to terpineol tested ranged from 1/0.025 to 1/400. The synergistic ratios of 4-sec-butylphenol to terpineol range from 1/1 to 1/5.

TABLE 17

First Component (A) = 3-tert-butylphenol
Second Component (B) = terpineol

| Microorganism | $C_a$ | $C_b$ | ΣFBC | Ratio A to B |
|---|---|---|---|---|
| E. coli 10536 | 0.3 | 0 | 1.00 |  |
|  | 0.3 | 0.025 | 1.04 | 1 to 0.08 |
|  | 0.3 | 0.05 | 1.08 | 1 to 0.17 |
|  | 0.3 | 0.075 | 1.13 | 1 to 0.25 |
|  | 0.4 | 0.1 | 1.50 | 1 to 0.25 |
|  | 0.08 | 0.3 | 0.77 | 1 to 3.75 |
|  | 0.1 | 0.3 | 0.83 | 1 to 3 |
|  | 0 | 0.6 | 1.00 |  |

The ratios of 3-tert-butylphenol to terpineol tested ranged from 1/0.025 to 1/400. The synergistic ratios of 3-tert-butylphenol to terpineol range from 1/3 to 1/3.75.

TABLE 18

First Component (A) = 2-hydroxydiphenylmethane
Second Component (B) = terpineol

| Microorganism | $C_a$ | $C_b$ | ΣFBC | Ratio A to B |
|---|---|---|---|---|
| E. coli 10536 | 0.6 | 0 | 1.00 |  |
|  | 0.4 | 0.025 | 0.71 | 1 to 0.06 |
|  | 0.5 | 0.025 | 0.88 | 1 to 0.05 |
|  | 0.5 | 0.05 | 0.92 | 1 to 0.1 |
|  | 0.2 | 0.075 | 0.46 | 1 to 0.38 |
|  | 0.3 | 0.075 | 0.63 | 1 to 0.25 |
|  | 0.4 | 0.075 | 0.79 | 1 to 0.19 |
|  | 0.5 | 0.075 | 0.96 | 1 to 0.15 |
|  | 0.2 | 0.1 | 0.50 | 1 to 0.5 |
|  | 0.3 | 0.1 | 0.67 | 1 to 0.33 |
|  | 0.4 | 0.1 | 0.83 | 1 to 0.25 |
|  | 0.2 | 0.3 | 0.83 | 1 to 1.5 |
|  | 0 | 0.6 | 1.00 |  |

The ratios of 2-hydroxydiphenylmethane to terpineol tested ranged from 1/0.025 to 1/400. The synergistic ratios of 2-hydroxydiphenylmethane to terpineol range from 1/0.05 to 1/1.5.

TABLE 19

First Component (A) = 4-hydroxydiphenylmethane
Second Component (B) = terpineol

| Microorganism | $C_a$ | $C_b$ | ΣFBC | Ratio A to B |
|---|---|---|---|---|
| E. coli 10536 | 0.5 | 0 | 1.00 |  |
|  | 0.3 | 0.025 | 0.64 | 1 to 0.08 |
|  | 0.4 | 0.025 | 0.84 | 1 to 0.06 |
|  | 0.4 | 0.05 | 0.88 | 1 to 0.13 |
|  | 0.3 | 0.075 | 0.73 | 1 to 0.25 |

TABLE 19-continued

First Component (A) = 4-hydroxydiphenylmethane
Second Component (B) = terpineol

| Microorganism | $C_a$ | $C_b$ | ΣFBC | Ratio A to B |
|---|---|---|---|---|
|  | 0.4 | 0.075 | 0.93 | 1 to 0.19 |
|  | 0.2 | 0.1 | 0.57 | 1 to 0.5 |
|  | 0.3 | 0.1 | 0.77 | 1 to 0.33 |
|  | 0.4 | 0.1 | 0.97 | 1 to 0.25 |
|  | 0.2 | 0.3 | 0.90 | 1 to 1.5 |
|  | 0 | 0.6 | 1.00 |  |

The ratios of 4-hydroxydiphenylmethane to terpineol tested ranged from 1/0.025 to 1/400. The synergistic ratios of 4-hydroxydiphenylmethane to terpineol range from 1/0.06 to 1/1.5.

TABLE 20

First Component (A) = 2-cyclopentylphenol
Second Component (B) = terpineol

| Microorganism | $C_a$ | $C_b$ | ΣFBC | Ratio A to B |
|---|---|---|---|---|
| E. coli 10536 | 0.8 | 0 | 1.00 |  |
|  | 0.6 | 0.025 | 0.79 | 1 to 0.04 |
|  | 0.6 | 0.05 | 0.83 | 1 to 0.08 |
|  | 0.5 | 0.075 | 0.75 | 1 to 0.15 |
|  | 0.6 | 0.075 | 0.88 | 1 to 0.13 |
|  | 0.5 | 0.1 | 0.79 | 1 to 0.2 |
|  | 0.6 | 0.1 | 0.92 | 1 to 0.17 |
|  | 0.3 | 0.3 | 0.88 | 1 to 1 |
|  | 0 | 0.6 | 1.00 |  |

The ratios of 2-cyclopentylphenol to terpineol tested ranged from 1/0.025 to 1/400. The synergistic ratios of 2-cyclopentylphenol to terpineol range from 1/0.04 to 1/1.

TABLE 21

First Component (A) = 4-cyclopentylphenol
Second Component (B) = terpineol

| Microorganism | $C_a$ | $C_b$ | ΣFBC | Ratio A to B |
|---|---|---|---|---|
| E. coli 10536 | 0.6 | 0 | 1.00 |  |
|  | 0.4 | 0.025 | 0.71 | 1 to 0.06 |
|  | 0.5 | 0.025 | 0.88 | 1 to 0.05 |
|  | 0.6 | 0.05 | 1.08 | 1 to 0.08 |
|  | 0.3 | 0.075 | 0.63 | 1 to 0.25 |
|  | 0.4 | 0.075 | 0.79 | 1 to 0.19 |
|  | 0.4 | 0.1 | 0.83 | 1 to 0.25 |
|  | 0.1 | 0.3 | 0.67 | 1 to 3 |
|  | 0.2 | 0.3 | 0.83 | 1 to 1.5 |
|  | 0 | 0.6 | 1.00 |  |

The ratios of 4-cyclopentylphenol to terpineol tested ranged from 1/0.025 to 1/400. The synergistic ratios of 4-cyclopentylphenol to terpineol range from 1/0.05 to 1/3.

The results of Examples 1 and 2 demonstrate that a synergistic antimicrobial effect of the monosubstituted phenols according to the invention and terpineol are obtained over a wide range of concentrations and ratios.

Example 3

The antimicrobial efficacy of compositions according to the invention, comprising a monosubstituted phenol (3-phenylphenol) and terpineol were tested following the same protocol and using the same terpineol as described for Example 1. The results are presented in Table 22.

TABLE 22

Antibacterial activity of 3-phenylphenol alone and
in combination with terpineol against *E. coli*

| Example | Mono-substituted phenol concentration $C_{(phenol)}$(% w/v) | Concentration of terpineol $C_{TERP}$(% w/v) | $N_{MBS}$ [log CFU/ml] | Standard deviation |
|---|---|---|---|---|
| 3:1* | 0.125% 3-phenylphenol | 0 | 4.3 | 0.4 |
| 3:2* | 0.05% 3-phenylphenol | 0 | 7.4 | 0.1 |
| 3:3* | 0.025% 3-phenylphenol | 0 | 7.7 | 0.1 |
| 3:4 X | 0.125% 3-phenylphenol | 0.15% alpha-terpineol | 0.0 | 0.0 |
| 3:5 Y | 0.05% 3-phenylphenol | 0.15% alpha-terpineol | 0.0 | 0.0 |
| 3:6 Z | 0.025% 3-phenylphenol | 0.15% alpha-terpineol | 0.0 | 0.0 |

*Examples marked with an asterisk (*) are comparative examples

By analogous reasoning as described for Example 1, it follows from comparative examples (3:1) to (3:3) that the MBC of 3-phenylphenol under the given conditions is at least 0.125% w/v. Similarly, ΣFBC values were calculated. As shown by the data in Table 23, Examples (3:5) and (3:6) demonstrate that 3-phenylphenol and terpineol are capable of synergistically providing antimicrobial action.

TABLE 23

Extent of synergistic interactions between binary compound
mixtures for compositions providing complete bacterial kill

| monosubstituted phenol | | | terpineol | | | Evidence |
|---|---|---|---|---|---|---|
| compound | Ex. | MBC % (w/v) | FBC[a] | MBC % (w/v) | FBC[b] | ΣFBC | of Synergy[c] |
| 3-phenylphenol | 3:5 | 0.125 | 0.4 | 0.4 | 0.38 | 0.78 | Yes |
| 3-phenylphenol | 3:6 | 0.125 | 0.2 | 0.4 | 0.38 | 0.58 | Yes |

[a]FBC of phenol: $C_{phenol}/MBC_{phenol}$
[b]FBC of terpineol: $C_{terpineol}/MBC_{terpineol}$
[c]Criterion for synergy: (ΣFBC <1)

Example 4

Automated Assessment of Efficacy in Surfactant Base

Sample Preparation

In these examples, the efficacy of combinations of monosubstituted phenols and terpineol were tested in a surfactant cleansing formulation comprising 2.85% sodium cocoyl glycinate and 1.85% sodium lauroamphoacetate. This corresponds to a 50% in use dilution with water of a typical neat formulation containing 5.7% cocoyl glycinate and 3.7% % sodium lauroamphoacetate during hand washing. Solutions were prepared such that the concentrations of the surfactant components and test actives were 1.1 times the final desired concentration in order to allow for dilution with the bacterial inoculum in the test. The solutions were manually adjusted to pH 10.0 by dropwise addition of sodium hydroxide solution, as measured with a pH meter at ambient temperature. Solutions of the monosubstituted phenols and/or terpineols were prepared at a maximum of 24 hours before testing. The same terpineol was used as in Example 1.

Test Methodology

The efficacy of the combinations of the present invention was determined against the same bacterium as in Example 1, *Escherichia coli* (*E. coli*—ATCC #10536), at a concentration of approximately $1 \times 10^8$ bacteria per mL.

Tests were conducted using standard microtiter plate assays using an automated liquid handling system. 270 µl of the surfactant test solution was pipetted into each well of the microtitre plate (Nunc F Gamma Irradiated 96F untreated microtitre plates of clear polystyrene) and 30 µl of the bacterial suspension was then added. After exactly 15 seconds of bacterial exposure, a 30 µl volume of bacterial cells was withdrawn and transferred to 270 µl of D/E quench solution. After 5 minutes in the D/E quench, the optical density (OD) was measured for each plate in turn at two specific wavelengths (450 nm and 590 nm). These provide a dual check of antimicrobial activity, as the $OD_{450}$ reading is specific for the yellow colour of D/E quench when bacterial growth is observed, whereas $OD_{590}$ is specific for the initial purple colour of the D/E quench which is retained if no bacterial growth is observed. After the time zero OD measurements, plates were then incubated at 37° C. overnight (16 hours) before repeating the OD measurements. Delta OD values were calculated by subtracting the OD values at 16 hours from the initial value at time zero from those at time=16 hours. Bacterial growth is observed as an increase in $OD_{450}$ and a decrease in $OD_{590}$. To identify antibacterially efficacious systems (those preventing appreciable bacterial growth after incubation), the following threshold changes in OD readings have been adopted: if (1). $OD_{450}$ increases by less than 0.2 absorbance unit (AU) on incubation and (2). $OD_{590}$ decreases by less than 0.35 AU on incubation. Conversely, where $OD_{450}$ increases by more than 0.1 AU and $OD_{590}$ decreases by more than 0.1 AU after incubation, corresponding to a colour shift from purple to yellow, the test system allows bacterial growth and is not deemed efficacious. Four replicate measurements in the same plate have been made for each test system. The number of replicate wells showing either bacterial growth or no growth is also readily assessed by eye by following the colour change. Thymol and terpineol were tested both alone and in combination for comparison purposes.

Dose responses for individual components and binary mixtures of actives at a fixed concentration ratio were generated by sequential dilution of liquors with further surfactant solution to obtain a series of endpoints ranging from 0.2 to 0.025% of the monosubstituted phenol and 0.5% to 0.0625% of the terpineol. In each case, binary mixtures were assessed in the weight to weight ratio monosubstituted phenol to terpineol of 1:2.5. In some selected cases, the combinations were also tested at the weight ratio 1:1.

TABLE 24

Antibacterial activities of thymol, or monosubstituted phenols alone, and in combination with terpineol in model surfactant solution

| Ex. | $C_{phenol}$ [a] (% w/v) | $C_{terpineol}$ [b] (% w/v) | DeltaOD (450 nm) [c] Mean | S.D. [f] | DeltaOD (590 nm) [d] Mean | S.D. [f] | $N_{rep}$ [e] |
|---|---|---|---|---|---|---|---|
| 4:1* | 0 | 0 | −0.60 | 0.02 | 0.64 | 0.02 | 4 |
| 4:2* | 0.2% thymol | 0 | −0.54 | 0.02 | 0.64 | 0.02 | 4 |
| 4:3* | 0.175% thymol | 0 | −0.54 | 0.02 | 0.56 | 0.02 | 4 |
| 4:4* | 0.15% thymol | 0 | −0.57 | 0.01 | 0.55 | 0.01 | 4 |
| 4:5* | 0.125% thymol | 0 | −0.58 | 0.01 | 0.55 | 0.01 | 4 |
| 4:6* | 0.1% thymol | 0 | −0.58 | 0.00 | 0.54 | 0.02 | 4 |
| 4:7* | 0.075% thymol | 0 | −0.59 | 0.01 | 0.54 | 0.01 | 4 |
| 4:8* | 0.05% thymol | 0 | −0.58 | 0.03 | 0.55 | 0.01 | 4 |
| 4:9* | 0.025% thymol | 0 | −0.55 | 0.01 | 0.65 | 0.02 | 4 |
| 4:10* | 0 | 0.5% | −0.45 | 0.02 | 0.64 | 0.02 | 4 |
| 4:11* | 0 | 0.4% | −0.47 | 0.01 | 0.59 | 0.00 | 4 |
| 4:12* | 0 | 0.35% | −0.48 | 0.01 | 0.58 | 0.01 | 4 |
| 4:13* | 0 | 0.3% | −0.51 | 0.01 | 0.57 | 0.01 | 4 |
| 4:14* | 0 | 0.25% | −0.54 | 0.01 | 0.56 | 0.1 | 4 |
| 4:15* | 0 | 0.2% | −0.56 | 0.01 | 0.55 | 0.01 | 4 |
| 4:16* | 0 | 0.15% | −0.57 | 0.01 | 0.55 | 0.01 | 4 |
| 4:17* | 0 | 0.1% | −0.53 | 0.02 | 0.67 | 0.02 | 4 |
| 4:18* | 0.2% 2-n-propylphenol | 0 | 0.27 | 0.01 | 0.22 | 0.01 | 0 |
| 4:19* | 0.175% 2-n-propylphenol | 0 | 0.22 | 0.03 | 0.20 | 0.01 | 0 |
| 4:20* | 0.15% 2-n-propylphenol | 0 | 0.20 | 0.03 | 0.17 | 0.02 | 0 |
| 4:21* | 0.125% 2-n-propylphenol | 0 | 0.18 | 0.03 | 0.16 | 0.01 | 0 |
| 4:22* | 0.1% 2-n-propylphenol | 0 | −0.49 | 0.02 | 0.58 | 0.01 | 4 |
| 4:23* | 0.075% 2-n-propylphenol | 0 | −0.46 | 0.02 | 0.57 | 0.01 | 4 |
| 4:24 | 0.2% 2-n-propylphenol | 0.5% | 0.26 | 0.01 | 0.26 | 0.00 | 0 |
| 4:25 | 0.175% 2-n-propylphenol | 0.4375% | 0.27 | 0.01 | 0.25 | 0.02 | 0 |
| 4:26 | 0.15% 2-n-propylphenol | 0.375% | 0.26 | 0.01 | 0.25 | 0.03 | 0 |
| 4:27 | 0.125% 2-n-propylphenol | 0.3125% | 0.26 | 0.02 | 0.25 | 0.02 | 0 |
| 4:28 | 0.1% 2-n-propylphenol | 0.25% | 0.26 | 0.02 | 0.24 | 0.02 | 0 |
| 4:29* | 0.075% 2-n-propylphenol | 0.1875% | −0.37 | 0.02 | 0.64 | 0.01 | 4 |
| 4:30* | 0.2% 3-n-propylphenol | 0 | −0.09 | 0.02 | 0.10 | 0.01 | 0 |
| 4:31* | 0.175% 3-n-propylphenol | 0 | −0.10 | 0.03 | 0.11 | 0.02 | 0 |
| 4:32* | 0.15% 3-n-propylphenol | 0 | −1.11 | 0.03 | 0.60 | 0.02 | 4 |
| 4:33* | 0.125% 3-n-propylphenol | 0 | −1.36 | 0.06 | 0.45 | 0.03 | 4 |
| 4:34* | 0.1% 3-n-propylphenol | 0 | −1.33 | 0.10 | 0.50 | 0.10 | 4 |
| 4:35 | 0.2% 3-n-propylphenol | 0.2% | −0.09 | 0.01 | 0.12 | 0.05 | 0 |
| 4:36 | 0.175% 3-n-propylphenol | 0.175% | −0.09 | 0.01 | 0.10 | 0.01 | 0 |
| 4:37 | 0.15% 3-n-propylphenol | 0.15% | −0.05 | 0.09 | 0.16 | 0.08 | 0 |
| 4:38 | 0.125% 3-n-propylphenol | 0.125% | −0.88 | 0.12 | 0.62 | 0.05 | 4 |
| 4:39 | 0.2% 3-n-propylphenol | 0.5% | −0.11 | 0.00 | 0.10 | 0.01 | 0 |
| 4:40 | 0.175% 3-n-propylphenol | 0.4375% | −0.04 | 0.06 | 0.14 | 0.06 | 0 |
| 4:41 | 0.15% 3-n-propylphenol | 0.375% | −0.07 | 0.06 | 0.10 | 0.01 | 0 |
| 4:42 | 0.125% 3-n-propylphenol | 0.3125% | −0.09 | 0.02 | 0.13 | 0.02 | 0 |
| 4:43 | 0.1% 3-n-propylphenol | 0.25% | −0.46 | 0.42 | 0.41 | 0.33 | 2 |
| 4:44 | 0.075% 3-n-propylphenol | 0.1875% | −1.25 | 0.03 | 0.54 | 0.01 | 4 |
| 4:45* | 0.2% 4-n-propylphenol | 0 | −0.51 | 0.02 | 0.66 | 0.02 | 4 |
| 4:46* | 0.175% 4-n-propylphenol | 0 | −0.54 | 0.02 | 0.57 | 0.02 | 4 |
| 4:47* | 0.15% 4-n-propylphenol | 0 | −0.56 | 0.02 | 0.54 | 0.02 | 4 |
| 4:48* | 0.125% 4-n-propylphenol | 0 | −0.56 | 0.01 | 0.55 | 0.02 | 4 |
| 4:49 | 0.2% 4-n-propylphenol | 0.5% | 0.21 | 0.03 | 0.28 | 0.02 | 0 |
| 4:50 | 0.175% 4-n-propylphenol | 0.4375% | 0.18 | 0.02 | 0.22 | 0.02 | 0 |
| 4:51 | 0.15% 4-n-propylphenol | 0.375% | 0.07 | 0.11 | 0.17 | 0.05 | 0 |
| 4:52* | 0.125% 4-n-propylphenol | 0.3125% | −0.30 | 0.39 | 0.67 | 0.25 | 4 |
| 4:53* | 0.2% 4-n-butylphenol | 0 | −0.51 | 0.01 | 0.64 | 0.02 | 4 |
| 4:54* | 0.175% 4-n-butylphenol | 0 | −0.55 | 0.03 | 0.54 | 0.03 | 4 |
| 4:55* | 0.15% 4-n-butylphenol | 0 | −0.55 | 0.01 | 0.54 | 0.02 | 4 |
| 4:56* | 0.125% 4-n-butylphenol | 0 | −0.58 | 0.01 | 0.53 | 0.02 | 4 |
| 4:57 | 0.2% 4-n-butylphenol | 0.5% | 0.17 | 0.01 | 0.25 | 0.03 | 0 |
| 4:58 | 0.175% 4-n-butylphenol | 0.4375% | 0.19 | 0.05 | 0.20 | 0.02 | 0 |
| 4:59 | 0.15% 4-n-butylphenol | 0.375% | −0.02 | 0.29 | 0.25 | 0.17 | 1 |
| 4:60* | 0.125% 4-n-butylphenol | 0.3125% | −0.49 | 0.01 | 0.55 | 0.03 | 4 |
| 4:61* | 0.2% 2-tert-butylphenol | 0 | −0.11 | 0.01 | 0.09 | 0.01 | 0 |
| 4:62* | 0.175% 2-tert-butylphenol | 0 | −0.11 | 0.12 | 0.14 | 0.06 | 0 |
| 4:63* | 0.15% 2-tert-butylphenol | 0 | −0.39 | 0.33 | 0.36 | 0.29 | 2 |
| 4:64* | 0.125% 2-tert-butylphenol | 0 | −1.23 | 0.17 | 0.54 | 0.09 | 4 |
| 4:65* | 0.1% 2-tert-butylphenol | 0 | −1.45 | 0.09 | 0.38 | 0.04 | 4 |
| 4:66* | 0.075% 2-tert-butylphenol | 0 | −1.48 | 0.13 | 0.40 | 0.13 | 4 |
| 4:67* | 0.05% 2-tert-butylphenol | 0 | −1.46 | 0.13 | 0.40 | 0.12 | 4 |
| 4:68 | 0.2% 2-tert-butylphenol | 0.2% | −0.09 | 0.02 | 0.10 | 0.02 | 0 |
| 4:69 | 0.175% 2-tert-butylphenol | 0.175% | −0.10 | 0.02 | 0.10 | 0.03 | 0 |
| 4:70 | 0.15% 2-tert-butylphenol | 0.15% | −0.10 | 0.01 | 0.10 | 0.01 | 0 |
| 4:71 | 0.125% 2-tert-butylphenol | 0.125% | −0.09 | 0.05 | 0.13 | 0.06 | 0 |
| 4:72 | 0.1% 2-tert-butylphenol | 0.1% | −0.88 | 0.59 | 0.54 | 0.16 | 3 |

TABLE 24-continued

Antibacterial activities of thymol, or monosubstituted phenols alone,
and in combination with terpineol in model surfactant solution

| Ex. | $C_{phenol}$ [a] (% w/v) | $C_{terpineol}$ [b] (% w/v) | DeltaOD (450 nm) [c] Mean | S.D. [f] | DeltaOD (590 nm) [d] Mean | S.D. [f] | $N_{rep}$ [e] |
|---|---|---|---|---|---|---|---|
| 4:73* | 0.075% 2-tert-butylphenol | 0.075% | −1.41 | 0.11 | 0.46 | 0.11 | 4 |
| 4:74 | 0.2% 2-tert-butylphenol | 0.5% | −0.12 | 0.01 | 0.10 | 0.01 | 0 |
| 4:75 | 0.175% 2-tert-butylphenol | 0.4375% | −0.11 | 0.01 | 0.10 | 0.01 | 0 |
| 4:76 | 0.15% 2-tert-butylphenol | 0.375% | −0.11 | 0.02 | 0.13 | 0.05 | 0 |
| 4:77 | 0.125% 2-tert-butylphenol | 0.3125% | −0.11 | 0.03 | 0.13 | 0.01 | 0 |
| 4:78 | 0.1% 2-tert-butylphenol | 0.25% | −0.09 | 0.06 | 0.12 | 0.01 | 0 |
| 4:79 | 0.075% 2-tert-butylphenol | 0.1875% | −0.43 | 0.65 | 0.24 | 0.12 | 1 |
| 4:80* | 0.05% 2-tert-butylphenol | 0.125% | −1.41 | 0.09 | 0.47 | 0.10 | 4 |
| 4:81* | 0.2% 3-tert-butylphenol | 0 | −1.39 | 0.05 | 0.44 | 0.05 | 4 |
| 4:82* | 0.175% 3-tert-butylphenol | 0 | −1.41 | 0.03 | 0.43 | 0.02 | 4 |
| 4:83* | 0.15% 3-tert-butylphenol | 0 | −1.46 | 0.05 | 0.41 | 0.04 | 4 |
| 4:84* | 0.125% 3-tert-butylphenol | 0 | −1.45 | 0.06 | 0.39 | 0.04 | 4 |
| 4:85* | 0.1% 3-tert-butylphenol | 0 | −1.48 | 0.08 | 0.37 | 0.04 | 4 |
| 4:86* | 0.075% 3-tert-butylphenol | 0 | −1.50 | 0.03 | 0.34 | 0.03 | 4 |
| 4:87 | 0.2% 3-tert-butylphenol | 0.2% | −0.11 | 0.00 | 0.09 | 0.01 | 0 |
| 4:88 | 0.175% 3-tert-butylphenol | 0.175% | −0.11 | 0.00 | 0.10 | 0.01 | 0 |
| 4:89 | 0.15% 3-tert-butylphenol | 0.15% | −0.72 | 0.51 | 0.47 | 0.23 | 3 |
| 4:90* | 0.125% 3-tert-butylphenol | 0.125% | −1.34 | 0.06 | 0.50 | 0.06 | 4 |
| 4:91 | 0.2% 3-tert-butylphenol | 0.5% | −0.12 | 0.01 | 0.10 | 0.01 | 0 |
| 4:92 | 0.175% 3-tert-butylphenol | 0.4375% | −0.10 | 0.03 | 0.11 | 0.01 | 0 |
| 4:93 | 0.15% 3-tert-butylphenol | 0.375% | −0.09 | 0.03 | 0.13 | 0.02 | 0 |
| 4:94 | 0.125% 3-tert-butylphenol | 0.3125% | −0.14 | 0.04 | 0.16 | 0.12 | 0 |
| 4:95 | 0.1% 3-tert-butylphenol | 0.25% | −0.62 | 0.49 | 0.45 | 0.25 | 2 |
| 4:96* | 0.075% 3-tert-butylphenol | 0.1875% | −1.34 | 0.08 | 0.47 | 0.05 | 4 |
| 4:97* | 0.2% 4-tert-butylphenol | 0 | −0.74 | 0.05 | 0.47 | 0.06 | 4 |
| 4:98* | 0.175% 4-tert-butylphenol | 0 | −0.71 | 0.08 | 0.41 | 0.06 | 4 |
| 4:99 | 0.2% 4-tert-butylphenol | 0.5% | 0.19 | 0.04 | 0.26 | 0.04 | 0 |
| 4:100* | 0.175% 4-tert-butylphenol | 0.4375% | −0.42 | 0.04 | 0.74 | 0.06 | 4 |
| 4:101* | 0.2% 2-sec-butylphenol | 0 | −0.46 | 0.01 | 0.64 | 0.02 | 4 |
| 4:102* | 0.175% 2-sec-butylphenol | 0 | −0.52 | 0.01 | 0.54 | 0.02 | 4 |
| 4:103* | 0.15% 2-sec-butylphenol | 0 | −0.55 | 0.02 | 0.53 | 0.02 | 4 |
| 4:104* | 0.125% 2-sec-butylphenol | 0 | −0.55 | 0.01 | 0.55 | 0.01 | 4 |
| 4:105 | 0.2% 2-sec-butylphenol | 0.5% | 0.24 | 0.02 | 0.24 | 0.03 | 0 |
| 4:106 | 0.175% 2-sec-butylphenol | 0.4375% | 0.19 | 0.04 | 0.19 | 0.01 | 0 |
| 4:107 | 0.15% 2-sec-butylphenol | 0.375% | 0.15 | 0.02 | 0.16 | 0.01 | 0 |
| 4:108* | 0.125% 2-sec-butylphenol | 0.3125% | −0.46 | 0.01 | 0.54 | 0.03 | 4 |
| 4:109* | 0.2% 4-sec-butylphenol | 0 | −0.50 | 0.02 | 0.64 | 0.02 | 4 |
| 4:110* | 0.175% 4-sec-butylphenol | 0 | −0.55 | 0.02 | 0.52 | 0.02 | 4 |
| 4:111* | 0.15% 4-sec-butylphenol | 0 | −0.55 | 0.02 | 0.54 | 0.02 | 4 |
| 4:112* | 0.125% 4-sec-butylphenol | 0 | −0.42 | 0.32 | 0.52 | 0.02 | 4 |
| 4:113 | 0.2% 4-sec-butylphenol | 0.5% | 0.19 | 0.02 | 0.26 | 0.02 | 0 |
| 4:114 | 0.175% 4-sec-butylphenol | 0.4375% | 0.18 | 0.04 | 0.19 | 0.02 | 0 |
| 4:115 | 0.15% 4-sec-butylphenol | 0.375% | −0.15 | 0.37 | 0.42 | 0.18 | 3 |
| 4:116 | 0.125% 4-sec-butylphenol | 0.3125% | −0.48 | 0.02 | 0.56 | 0.02 | 4 |
| 4:117* | 0.2% 4-pentylphenol | 0 | −0.51 | 0.01 | 0.61 | 0.02 | 4 |
| 4:118 | 0.2% 4-pentylphenol | 0.5% | −0.41 | 0.02 | 0.63 | 0.03 | 4 |
| 4:119* | 0.2% 4-hexylphenol | 0 | −0.50 | 0.02 | 0.62 | 0.03 | 4 |
| 4:120* | 0.2% 4-hexylphenol | 0.5% | −0.43 | 0.02 | 0.64 | 0.02 | 4 |
| 4:121* | 0.2% 3-phenylphenol | 0 | −0.65 | 0.05 | 0.48 | 0.05 | 4 |
| 4:122* | 0.175% 3-phenylphenol | 0 | −0.68 | 0.08 | 0.43 | 0.03 | 4 |
| 4:123* | 0.15% 3-phenylphenol | 0 | −0.61 | 0.03 | 0.48 | 0.03 | 4 |
| 4:124* | 0.125% 3-phenylphenol | 0 | −0.62 | 0.02 | 0.49 | 0.02 | 4 |
| 4:125* | 0.1% 3-phenylphenol | 0 | −0.61 | 0.02 | 0.51 | 0.01 | 4 |
| 4:126 | 0.2% 3-phenylphenol | 0.5% | 0.27 | 0.02 | 0.24 | 0.02 | 0 |
| 4:127 | 0.175% 3-phenylphenol | 0.4375% | 0.23 | 0.06 | 0.22 | 0.04 | 0 |
| 4:128 | 0.15% 3-phenylphenol | 0.375% | 0.16 | 0.10 | 0.22 | 0.05 | 0 |
| 4:129 | 0.125% 3-phenylphenol | 0.3125% | −0.15 | 0.38 | 0.49 | 0.18 | 2 |
| 4:130 | 0.1% 3-phenylphenol | 0.25% | −0.46 | 0.08 | 0.64 | 0.05 | 4 |
| 4:131* | 0.2% 2-benzylphenol | 0 | −0.44 | 0.03 | 0.67 | 0.63 | 4 |
| 4:132* | 0.175% 2-benzylphenol | 0 | −0.44 | 0.01 | 0.62 | 0.60 | 4 |
| 4:133* | 0.15% 2-benzylphenol | 0 | −0.47 | 0.03 | 0.58 | 0.57 | 4 |
| 4:134* | 0.125% 2-benzylphenol | 0 | −0.50 | 0.02 | 0.56 | 0.55 | 4 |
| 4:135* | 0.1% 2-benzylphenol | 0 | −0.52 | 0.03 | 0.56 | 0.54 | 4 |
| 4:136* | 0.075% 2-benzylphenol | 0 | −0.52 | 0.03 | 0.57 | 0.55 | 4 |
| 4:137* | 0.05% 2-benzylphenol | 0 | −0.54 | 0.03 | 0.61 | 0.60 | 4 |
| 4:138 | 0.2% 2-benzylphenol | 0.5% | 0.09 | 0.03 | 0.10 | 0.04 | 0 |
| 4:139 | 0.175% 2-benzylphenol | 0.4375% | 0.14 | 0.03 | 0.16 | 0.01 | 0 |
| 4:140 | 0.15% 2-benzylphenol | 0.375% | 0.10 | 0.09 | 0.15 | 0.03 | 0 |
| 4:141 | 0.125% 2-benzylphenol | 0.3125% | 0.09 | 0.02 | 0.10 | 0.01 | 0 |
| 4:142 | 0.1% 2-benzylphenol | 0.25% | −0.03 | 0.34 | 0.29 | 0.21 | 2 |
| 4:143 | 0.075% 2-benzylphenol | 0.1875% | −0.26 | 0.39 | 0.43 | 0.19 | 3 |
| 4:144 | 0.05% 2-benzylphenol | 0.125% | −0.50 | 0.04 | 0.56 | 0.00 | 4 |

TABLE 24-continued

Antibacterial activities of thymol, or monosubstituted phenols alone, and in combination with terpineol in model surfactant solution

| Ex. | $C_{phenol}$ [a] (% w/v) | $C_{terpineol}$ [b] (% w/v) | DeltaOD (450 nm) [c] Mean | S.D. [f] | DeltaOD (590 nm) [d] Mean | S.D. [f] | $N_{rep}$ [e] |
|---|---|---|---|---|---|---|---|
| 4:145* | 0.2% 4-benzylphenol | 0 | −0.55 | 0.02 | 0.62 | 0.03 | 4 |
| 4:146* | 0.175% 4-benzylphenol | 0 | −0.53 | 0.02 | 0.63 | 0.03 | 4 |
| 4:147* | 0.15% 4-benzylphenol | 0 | −0.53 | 0.01 | 0.64 | 0.02 | 4 |
| 4:148* | 0.125% 4-benzylphenol | 0 | −0.55 | 0.02 | 0.64 | 0.03 | 4 |
| 4:149 | 0.2% 4-benzylphenol | 0.5% | 0.21 | 0.03 | 0.28 | 0.04 | 0 |
| 4:150 | 0.175% 4-benzylphenol | 0.4375% | 0.18 | 0.03 | 0.22 | 0.01 | 0 |
| 4:151 | 0.15% 4-benzylphenol | 0.375% | −0.14 | 0.36 | 0.38 | 0.22 | 2 |
| 4:152 | 0.125% 4-benzylphenol | 0.3125% | −0.48 | 0.02 | 0.64 | 0.03 | 4 |
| 4:153* | 0.2% 2-cyclopentyl-phenol | 0 | −1.55 | 0.04 | 0.36 | 0.33 | 4 |
| 4:154* | 0.175% 2-cyclopentyl-phenol | 0 | −1.58 | 0.07 | 0.39 | 0.33 | 4 |
| 4:155* | 0.15% 2-cyclopentyl-phenol | 0 | −1.61 | 0.07 | 0.34 | 0.30 | 4 |
| 4:156* | 0.125% 2-cyclopentyl-phenol | 0 | −1.58 | 0.08 | 0.36 | 0.31 | 4 |
| 4:157* | 0.1% 2-cyclopentyl-phenol | 0 | −1.57 | 0.10 | 0.40 | 0.30 | 4 |
| 4:158 | 0.2% 2-cyclopentyl-phenol | 0.5% | −0.12 | 0.01 | 0.10 | 0.01 | 0 |
| 4:159* | 0.175% 2-cyclopentyl-phenol | 0.4375% | −0.11 | 0.01 | 0.10 | 0.01 | 0 |
| 4:160 | 0.15% 2-cyclopentyl-phenol | 0.375% | −0.12 | 0.01 | 0.12 | 0.02 | 0 |
| 4:161 | 0.125% 2-cyclopentyl-phenol | 0.3125% | −0.41 | 0.35 | 0.40 | 0.33 | 2 |
| 4:162 | 0.1% 2-cyclopentyl-phenol | 0.25% | −1.28 | 0.11 | 0.53 | 0.06 | 4 |
| 4:163* | 0.2% 4-cyclopentyl-phenol | 0 | −0.48 | 0.01 | 0.66 | 0.03 | 4 |
| 4:164* | 0.175% 4-cyclopentyl-phenol | 0 | −0.48 | 0.02 | 0.57 | 0.02 | 4 |
| 4:165 | 0.2% 4-cyclopentyl-phenol | 0.5% | 0.04 | 0.28 | 0.36 | 0.15 | 1 |
| 4:166 | 0.175% 4-cyclopentyl-phenol | 0.4375% | −0.41 | 0.01 | 0.63 | 0.02 | 4 |
| 4:167* | 0.2% (E)-2-(prop-1-enyl)-phenol | 0 | −1.29 | 0.05 | 0.52 | 0.03 | 4 |
| 4:168* | 0.175% (E)-2-(prop-1-enyl)-phenol | 0 | −1.41 | 0.03 | 0.43 | 0.02 | 4 |
| 4:169* | 0.15% (E)-2-(prop-1-enyl)-phenol | 0 | −1.43 | 0.04 | 0.40 | 0.03 | 4 |
| 4:170* | 0.125% (E)-2-(prop-1-enyl)-phenol | 0 | −1.45 | 0.02 | 0.39 | 0.02 | 4 |
| 4:171* | 0.1% (E)-2-(prop-1-enyl)-phenol | 0 | −1.45 | 0.02 | 0.39 | 0.01 | 4 |
| 4:172* | 0.075% (E)-2-(prop-1-enyl)-phenol | 0 | −1.44 | 0.03 | 0.39 | 0.01 | 4 |
| 4:173 | 0.2% (E)-2-(prop-1-enyl)-phenol | 0.2% | −0.11 | 0.10 | 0.10 | 0.01 | 0 |
| 4:174 | 0.175% (E)-2-(prop-1-enyl)-phenol | 0.175% | −0.08 | 0.05 | 0.12 | 0.05 | 0 |
| 4:175 | 0.15% (E)-2-(prop-1-enyl)-phenol | 0.15% | −0.80 | 0.50 | 0.56 | 0.30 | 3 |
| 4:176 | 0.125% (E)-2-(prop-1-enyl)-phenol | 0.125% | −1.27 | 0.08 | 0.57 | 0.05 | 4 |
| 4:177 | 0.2% (E)-2-(prop-1-enyl)-phenol | 0.5% | −0.11 | 0.01 | 0.10 | 0.01 | 0 |
| 4:178 | 0.175% (E)-2-(prop-1-enyl)-phenol | 0.4375% | −0.11 | 0.02 | 0.11 | 0.01 | 0 |
| 4:179 | 0.15% (E)-2-(prop-1-enyl)-phenol | 0.375% | −0.11 | 0.01 | 0.12 | 0.01 | 0 |
| 4:180 | 0.125% (E)-2-(prop-1-enyl)-phenol | 0.3125% | −0.12 | 0.01 | 0.12 | 0.01 | 0 |
| 4:181 | 0.1% (E)-2-(prop-1-enyl)-phenol | 0.25% | −0.35 | 0.49 | 0.28 | 0.28 | 1 |
| 4:182 | 0.075% (E)-2-(prop-1-enyl)-phenol | 0.1875% | −1.27 | 0.05 | 0.58 | 0.04 | 4 |

*Examples marked with an asterisk (*) are comparative examples
[a] Concentration of thymol or monosubstituted phenol as specified
[b] Concentration of terpineol
[c] DeltaOD (450 nm) = $OD_{450}$ (time = 16 hours) − $OD_{450}$ (time zero)
[d] DeltaOD (590 nm) = $OD_{590}$ (time = 16 hours) − $OD_{590}$ (time zero)
[e] $N_{rep}$ = No. of replicates showing growth (out of 4)
[f] S.D. = standard deviation

TABLE 25

Minimum biocidal concentrations of antimicrobial
components in 2.85% sodium cocoyl glycinate +
1.85% sodium, lauroamphoacetate solution at pH 10

| Component | MBC (% w/v) |
|---|---|
| Thymol | >0.2 |
| alpha-terpineol | >0.5 |
| 2-n-propylphenol | 0.125 |
| 3-n-propylphenol | 0.175 |
| 4-n-propylphenol | >0.2 |
| 4-n-butylphenol | >0.2 |
| 2-tert-butylphenol | 0.175 |
| 3-tert-butylphenol | >0.2 |
| 4-tert-butylphenol | >0.2 |
| 2-sec-butylphenol | >0.2 |
| 4-sec-butylphenol | >0.2 |
| 4-pentylphenol | >0.2 |
| 3-phenylphenol | >0.2 |
| 2-benzylphenol | >0.2 |
| 4-benzylphenol | >0.2 |
| 2-cyclopentylphenol | >0.2 |
| 4-cyclopentylphenol | >0.2 |
| (E)-2-(prop-1-enyl)phenol | >0.2 |

Results

The surfactants used are not themselves antimicrobially active against *E. coli* at the concentrations employed as shown by the results of Ex. (4:1) in Table 24. Thus, any antimicrobial efficacy can be ascribed to the monosubstituted phenols and/or terpineol. Table 25 presents MBC-values determined similarly as described for Example 1. Many of the tested monosubstituted phenols have an MBC higher than the highest tested concentrations, in the presence of the specified surfactants.

The results of Table 24 show that with the exceptions of 4-cyclopentylphenol, 4-pentylphenol and 4-hexylphenol, all the monosubstituted phenols tested show 15 second bactericidal efficacy (complete kill in all 4 replicates) against *E. coli* when tested in combination with alpha-terpineol at concentrations lower than their MBC in the same surfactant formulation (comprising cocoyl glycinate and lauroamphoacetate). This is true for both for the 1:1 and 1:2.5 mono-substituted phenol: alpha terpineol ratios but efficacy is maintained at lower monosubstituted phenol concentrations when the higher ratio of alpha-terpineol is present. 4-Hexylphenol is a comparative monosubstituted phenol.

Thus, it was found that monosubstituted phenols according to the invention and in particular 2-n-propylphenol. 3-n-propylphenol, 4-n-propylphenol, 4-n-butylphenol, 2-tert-butylphenol, 3-tert-butylphenol, 4-tert-butylphenol, 2-sec-butylphenol, 4-sec-butylphenol, 3-phenylphenol, 2-benzylphenol, 4-benzylphenol, 2-cyclopentylphenol, (E)-2-(prop-1-enyl)phenol show enhanced antimicrobial action in combination with terpineol in the presence of surfactant, in particular cocoyl glycinate and lauroamphoacetate.

The invention claimed is:

1. A synergistic antimicrobial composition comprising:
   i. a monosubstituted phenol selected from the group consisting of (E)-2-(prop-1-enyl)phenol, 4-pentylphenol, 3-tert-butylphenol, 2-hydroxydiphenylmethane, 4-hydroxydiphenylmethane, 2-cyclopentylphenol and 4-cyclopentylphenol; and
   ii. terpineol wherein a weight ratio of (E)-2-(prop-1-enyl)phenol to terpineol is from 1:0.13 to 1:1, a weight ratio of 4-pentylphenol to terpineol is from 1:0.17 to 1:3, a weight ratio of 3-tert-butylphenol to terpineol is from 1:3 to 1:3.75, a weight ratio of 2-hydroxydiphenylmethane to terpineol is from 1:0.05 to 1:0.1 or 1:0.19 to 1:0.5, a weight ratio of 4-hydroxydiphenylmethane to terpineol is from 1:0.06 to 1:0.13 or 1:0.33 to 1:1.5, a weight ratio of 2-cyclopentylphenol to terpineol is from 1:0.04 to 1:1 and a weight ratio of 4-cyclopentylphenol to terpineol is from 1:0.19 to 1:3.

2. A synergistic antimicrobial composition consisting essentially of:
   i. a monosubstituted phenol selected from the group consisting of 3-n-propylphenol, 4-n-butylpenol and 4-sec-butylphenol; and
   ii. terpineol wherein a weight ratio of 3-n-propylphenol to terpineol is from 1:0.33 to 1:3.75, a weight ratio of 4-n-butylphenol to terpineol is from 1:0.5 to 1:6 and a weight ratio of 4-sec-butylphenol to terpineol is from 1:1 to 1:3.75.

* * * * *